United States Patent
Rahme

(10) Patent No.: US 6,511,500 B1
(45) Date of Patent: Jan. 28, 2003

(54) USE OF AUTONOMIC NERVOUS SYSTEM NEUROTRANSMITTERS INHIBITION AND ATRIAL PARASYMPATHETIC FIBERS ABLATION FOR THE TREATMENT OF ATRIAL ARRHYTHMIAS AND TO PRESERVE DRUG EFFECTS

(76) Inventor: Marc Mounir Rahme, 5128 Bowden Ave., San Diego, CA (US) 92117

( * ) Notice: Subject to any disclaimer, the term of this patent is extended or adjusted under 35 U.S.C. 154(b) by 191 days.

(21) Appl. No.: 09/588,866

(22) Filed: Jun. 6, 2000

(51) Int. Cl.$^7$ ................................................ A61N 1/00
(52) U.S. Cl. ........................................................ 607/1
(58) Field of Search ........................................ 607/1–60

(56) References Cited

U.S. PATENT DOCUMENTS

| | | | |
|---|---|---|---|
| 5,330,507 A | * | 7/1994 | Schwartz |
| 5,690,681 A | * | 11/1997 | Geddes et al. |
| 5,700,282 A | * | 12/1997 | Zabara |
| 6,292,695 B1 | * | 9/2001 | Webster et al. |

* cited by examiner

Primary Examiner—Scott M. Getzow

(57) ABSTRACT

Atrial arrhythmias, a major contributor to cardiovascular morbidity, are believed to be influenced by autonomic nervous system tone. The main purpose of this invention was to highlight new findings that have emerged in the study of effects of autonomic nervous system tone on atrial arrhythmias, and its interaction with class III antiarrhythmic drug effects. This invention evaluates the significance of sympathetic and parasympathetic activation by determining the effects of autonomic nervous system using a vagal and stellar ganglions stimulation, and by using autonomic nervous system neurotransmitters infusion (norepinephrine, acetylcholine). This invention evaluates the autonomic nervous system effects on the atrial effective refractory period duration and dispersion, atrial conduction velocity, atrial wavelength duration, excitable gap duration during a stable circuit (such atrial flutter circuit around an anatomical obstacle), and on the susceptibility of occurrence (initiation, maintenance and termination) of atrial re-entrant arrhythmias in canine. This invention also evaluates whether autonomic nervous system activation effects via a local neurotransimitters infusion into the right atria can alter those of class III antiarrhythmic drug, sotalol, during a sustained right atrial flutter. This invention represents an emergent need to set-up and develop a new class of anti-cholinergic drug therapy for the treatment of atrial arrhythmias and to combine this new anti-cholinergic class to antiarrhythmic drugs. Furthermore, this invention also highlights the importance of a local application of parasympathetic neurotransmitters/blockers and a catheter ablation of the area of right atrium with the highest density of parasympathetic fibers innervation. This may significantly reduce the occurrence of atrial arrhythmias and may preserve the antiarrhythmic effects of any drugs used for the treatment of atrial re-entrant arrhythmias.

8 Claims, No Drawings

USE OF AUTONOMIC NERVOUS SYSTEM NEUROTRANSMITTERS INHIBITION AND ATRIAL PARASYMPATHETIC FIBERS ABLATION FOR THE TREATMENT OF ATRIAL ARRHYTHMIAS AND TO PRESERVE DRUG EFFECTS

FIELD OF THE INVENTION

Cardiac rhythm disturbances are a major cause of morbidity and even mortality in our ageing population. Most of these rhythms are based on reentry, i.e. the continuous circulation of a wavefront of excitation around a functional or anatomical circuit such atrial fibrillation and flutter. Atrial fibrillation could exist as a stable state, self-sustained and independent of its initiating trigger in the presence of non-uniform distribution (i.e. dispersion) of atrial refractory periods. In addition, maintenance of atrial fibrillation may require a critically short wavelength in order to sustain reentry. However, the cellular and pathophysiological mechanisms in the initiation and maintenance of atrial fibrillation remain poorly understood. It has been reported that inducibility and maintenance of this atrial arrhythmia are associated with an increased dispersion in atrial refractoriness. In addition, alterations in the electrophysiologic properties of the atria affecting wavelength may led to persistence of atrial fibrillation and to the occurrence of reentrant atrial arrhythmias in both in vitro and in vivo models. Furthermore, electrical remodeling of the atria may also increase the likelihood to the maintenance of this atrial arrhythmia.

Electrophysiological studies suggest that the mechanism of type I atrial flutter in humans and in canine models involves a macroreentrant circuit around an anatomically or anisotropically defined obstacle with either a partially or fully excitable gap. The excitable gap is one of the determinant of the continued circulation of the abnormal atrial impulse and in its presence an extrastimulus may excite the circuit and reset the tachycardia. Furthermore, the persistent circulation of this wavefront is determined by the effective refractory period, the conduction velocity, the wavefront and the nature and duration of the excitable gap, i.e. that portion of the circuit which has partially or fully recovered its excitability. This excitable gap, in part, determined by the size of the reentry circuit and the electrophysiological properties of its tissue components.

However, external influences may also significantly modify the susceptibility for the occurrence of atrial arrhythmias via different electrophysiological mechanisms such as the excitable gap characteristics, the effective refractory period duration and dispersion, the conduction velocity, the wavefront duration and propagation forms and the number of the wavelets. Autonomic nervous system tone may implicitly have a role in the pathogenesis of initiation and persistence of supraventricular arrhythmias. In experimental models, both vagal stimulation and acetylcholine application to the heart can nonhomogeneously shorten atrial refractory period and produce either paroxysmal atrial arrhythmia, flutter or fibrillation. In man, the onset of atrial fibrillation has a diurnal distribution with a statistically significant peak occurring at night which correlates with an immediately preceding increase in vagal drive. Catecholamine administration (Isoproterenol) also shortens the atrial action potential and stimulation of sympathetic nerves shortens atrial refractoriness and increases its dispersion facilitating the induction of atrial fibrillation. In man, attacks of atrial fibrillation have also been reported to be associated with adrenergic activation. Little is known, however, on the possible influence of autonomic nervous system tone on an established stable reentry circuit such as is seen in atrial flutter, an arrhythmia which is frequently difficult to interrupt by pharmacological means, and also on the occurrence of the leading circle phenomena during atrial fibrillation episodes. In a human study of parasympathetic and sympathetic blockade, observations limited to effects on atrial flutter cycle length did not detect any change either in the supine or upright position. No study has yet addressed the effects of autonomic neurotransmitters on the refractory period, duration and composition of the excitable gap and thus, on the viability of an atrial reentry circuit.

Despite considerable advances in our understanding on the mechanism of this atrial arrhythmia, antiarrhythmic drug therapy to produce and maintain sinus rhythm is fraught with a variety of problems. These drugs are either incompletely effective, may have proarrhythmic properties, and also may increase mortality. Since some of the more dangerous proarrhythmic potential of antiarrhythmic drugs appears to be related to sodium channel blocking properties, there has been increased interest in class III drugs, which act by increasing action potential duration and refractoriness without blocking sodium channels. The pharmacological control of cardiac arrhythmias using class III antiarrhythmic drugs which prolong the cardiac action potential has gained interest recently, particularly in view of reports of proarrhythmic and increased mortality associated with the use of class I antiarrhythmic drugs in the treatment of both ventricular and atrial arrhythmias. In addition, there is evidence that drugs with class III antiarrhythmic action may be more effective than the class I antiarrhythmic drugs for conversion and suppression of some cardiac arrhythmias, particularly those due to reentry. This greater efficacy of the class III antiarrhythmic drugs may be due in part to their ability to selectively prolong refractoriness and wavelength and reduce dispersion of refractoriness. Despite extensive investigation in the past, the critical electrophysiologic determinants of antiarrhythmic drug efficacy in specific reentrant tachycardias are not fully delineated. Sotalol is one such class III antiarrhythmic drugs which can exist in either the d- or l-isomer forms. Both isomers have equal class III activity but only the l-isomer possesses significant β-adrenoceptor blocking activity. d,l-Sotalol, the racemic, therefore has both class II and class III properties. It has been used both to terminate atrial arrhythmias and to prevent their recurrence following cardioversion. It blocks both the slow and rapid component of the delayed rectifier potassium current ($I_{ks}$ and $I_{kr}$) and thus increases the atrial action potential duration and the atrial effective refractory period. At high concentrations, Sotalol can also inhibit the background or inward rectifying K$^+$ ($I_{k1}$) and decreases the transient outward K$^+$ current ($I_{to}$). Administration of class III antiarrhythmic drugs has been reported to prevent and/or terminate atrial flutter and fibrillation, an effect correlated with a shortening of the excitable gap and with prolongation of both the atrial arrhythmias cycle length and the refractory period.

The purpose of this invention is to determine the effects of norepinephrine and acetylcholine on the excitable gap composition during a sustained stable atrial flutter, and on the atrial effective refractory period duration and dispersion, atrial conduction velocity and atrial wavelength. Furthermore, this invention illustrates also the influence of autonomic nervous system activation and neurotransmitters infusion on the occurrence of these atrial arrhythmias, and whether these significant effects could alter those of sotalol on the same electrophysiological parameters. This invention also project the possibility for new atrial targets for the use of catheter ablation during the treatment of atrial arrhythmias. These new targets for catheter ablation during an atrial arrhythmia may be the fully excitable tissue, and/or the areas with the greatest density of parasympathetic innervation such as the tissues near the sinoatrial nodal fat pad and septal.

BRIEF SUMMARY OF THE INVENTION

Atrial arrhythmias, a major contributor to cardiovascular morbidity, are believed to be influenced, activated and aggravated by autonomic nervous system tone. Furthermore, the treatment of this atrial arrhythmias are influenced, threaded and degenerated to a proarrhythmic events under the dominant effects of the autonomic nervous system activation. This invention evaluated the significance of sympathetic and parasympathetic activation by determining the effects of norepinephrine and acetylcholine on the composition of the excitable gap during a stable sustained atrial flutter, on the effective refractory period, on the conduction velocity, and on the wavelength in a canine model of stable atrial flutter. We also evaluated whether norepinephrine and acetylcholine administration can alter class III antiarrhythmic drug effects in the occurrence of atrial arrhythmias. This invention also evaluated the significance of sympathetic and parasympathetic denervation and activation by determining the direct effects of right and left stellar ganglions (10 Hz, 2 ms) and right vagal (1 Hz, 0.1 ms) stimulation on the atrial effective refractory period duration and dispersion, on the atrial conduction velocity, on the atrial wavelength and on the viability of the occurrence of atrial fibrillation. This invention also evaluated whether the autonomic nervous stimulation can alter class III antiarrhythmic drug (sotalol) effects in the same electrophysiological parameters described above and on the occurrence of these atrial arrhythmias.

In a group of 13 open chest anaesthetised dogs, atrial flutter model was produced during baseline conditions around the tricuspid valve using a Y-shaped lesion in the intercaval area extending to the right atrial appendage. Atrial flutter was induced at the shortest effective refractory period site using fast pacing stimulation (S1S1) of 100–150 ms. This manoeuvre was repeated as much as necessary with more damage in the Y-shaped lesion model to achieve a sustained stable atrial flutter (>10 min) during the baseline conditions. In order to determine the excitable gap duration and composition during this sustained and stable atrial flutter, a diastole was scanned with a single premature extrastimulus, S1S2 (S1S2=]refractory period, flutter cycle length[) to define the atrial flutter circuit composition and duration (flutter cycle length=refractory period+excitable gap). Atrial flutter cycle length, atrial effective refractory period and duration of the excitable gap were then determined. Measures were repeated during a constant infusion into the right coronary artery of norepinephrine (15 μg/min) and acetylcholine (2 μg/min) allowing 15 min for recovery from norepinephrine effects. The effects of norepinephrine and acetylcholine at a constant plasma level of d-sotalol or d,l-sotalol (0.8 mg/kg+0.4 mg/kg/hr) were also studied in 2 different groups of chloralose anaesthetised dogs on the same electrophysiological parameters described above.

In a group of 14 anaesthetised open chest dogs, atrial fibrillation was induced by fast pacing and up to 10 attempts of arrhythmia initiations during baseline condition, vagal denervation, right and left vagal stimulation #1 (1 Hz, 0.1 ms), right and left stellar ganglions denervation, right and left vagal stimulation #2 (1 Hz, 0.1 ms), right and left stellar ganglions stimulation (10 Hz, 2 ms), and right and left vagal stimulation (1 Hz, 0.1 ms) associated with right and left stellar ganglions stimulation (10 Hz, 2 ms). Under the same conditions described above, the effective refractory period duration and dispersion (at S1S1=200 ms), the conduction velocity and the wavelength are determined. Atrial fibrillation occurrence was evaluated by the mean duration of 10 atrial fibrillation episodes at baseline (for a group of animals when none of the 10 atrial fibrillation episodes at baseline were lasting more than 3 minutes) and following each of the conditions described above.

In summary, both neurotransmitters infusions (acetylcholine>>norepinephrine) significantly increased the occurrence of the initiation of atrial flutter and decreased the duration of its maintenance by rapid (less than 2 minutes) conversion to a non sustained atrial fibrillation and then to a sinus rhythm state. Both neurotransmitters significantly increased the safety margin of excitability ahead of the wavefront and decreased the effective refractory. Autonomic and, in particular, vagal effects significantly diminish the action of pure class III antiarrhythmic drug, d-sotalol. However, in the presence of d,l-sotalol, a class III combined with anti-adrenergic effects, only acetylcholine still completely reversed its electrophysiological effects. This suggests that class III antiarrhythmic drugs with class II properties could resist the effects of sympathetic but not that of vagal activation. The effects of autonomic nervous system stimulation also significantly increased the occurrence of atrial fibrillation initiation and persistence. The effects of vagus activation significantly exceed those of sympathetic on the occurrence of atrial fibrillation, on the atrial effective refractory period duration and dispersion, on the conduction velocity and on the wavelength. In a particular interest, when the stellar ganglions denervation facilitates the occurrence of the initiation of a non sustained atrial fibrillation following the premature stimulation (S1S2) (data described the relation between initiation vs. duration of atrial fibrillation are not presented in this invention), the vagal denervation significantly reduced its initiation and maintenance. Furthermore, in the presence of class III drug therapy, the vagal stimulation significantly and markedly reversed the antiarrhythmic therapeutic effects of d,l-sotalol. These results demonstrate an absolute and emergent need to consider the effects of the presence and of the activation of parasympathetic nervous system tone during the pharmacological treatment of atrial arrhythmias. In addition, this invention targets the areas with the greatest density of parasympathetic innervation for ablation, such as the areas located near the sinoatrial nodal fat pad and septal, for the treatment of atrial arrhythmias during a catheter ablation manner.

DETAILED DESCRIPTION OF THE INVENTION

The main purpose of this invention was to study the significant effects of autonomic nervous system on the atrial electrophysiologic parameters related to the preconditioning, initiation, persistence and termination of atrial fibrillation and flutter. Furthermore, this invention evaluated whether the significant effects of autonomic nervous system on the atrial electrophysiological parameters and on the occurrence of atrial arrhythmias could change those of class III antiarrhythmic drugs.

Autonomic Nervous System Effects on Atrial Tissue

The effects of sympathetic neural activity on the heart are gradually developed and receded, whereas the inhibitory effects of vagal activity appear and disappear rapidly. The automatic cells in the heart respond promptly to vagal stimulation within a steady-state value of two cardiac cycles. The ability of the vagus nerves to regulate heart rate beat by beat could be explained by the speed at which the neural signal is rapidly transduced to a cardiac response and by also by the rapidity of the processes that restore the basal heart rate when vagal activity ceases. The mechanisms of this rapid development of vagal effects on heart rate will be related to: 1) the acetylcholine regulated potassium channels; 2) the hyperpolarization activated channels, which conduct the If current; and 3) the calcium channels. The acetylcholine and the If channels could both respond rapidly to vagal activity. The If and Ica channels are directly involved in generating the slow diastolic depolarisation in sinus node cells. The release of acetylcholine interacts with cardiac muscarinic receptors that are coupled to its regulated potassium channels directly through G proteins without an interaction of a slow second messenger system. These potassium channels are fully activated by this release of acetylcholine within a few milliseconds. The relatively slow development of the sympathetic responses has been attributed mainly to the inclusion of a second messenger system, notably the adenylyl cyclase system, in the cascade of events that transduce the neuronal release of norepinephrine into a change in cardiac performance. The chronotropic response of the heart to sympathetic activation is mediated mainly via several types of ion channels, such as Ica and If currents. This second messenger system is too slow to permit beat-by-beat regulation of cardiac function. The norepinephrine released from the sympathetic nerve endings is removed from the cardiac tissues much more slowly than is the acetylcholine that is released from the vagal terminals. Then, the atrial tissue and the related ionic currents (Ica, If) are submitted to the sympathetic neural activity after a certain delay of ganglion stellar stimulation. Furthermore, during the study of vagal-sympathetic interaction, the on-set effects of sympathetic stimulation are considered in the presence of existing vagal stimulation effects on atrial tissue and not in the on-set of this vagal stimulation effects.

Autonomic Nervous System Effects in Atrial Arrhythmias

Recently, it has become increasingly recognised that beyond an understanding of the electrophysiological behaviour of an isolated reentry circuit, it is necessary also to be aware of possible external influences on the atrial arrhythmias occurrence and on the related atrial electrophysiological parameters such as the effective refractory period duration and dispersion, the conduction velocity, the wavelength and the excitable tissue during these atrial arrhythmias. Variations of autonomic tone have been hypothesised to have a role in the pathogenesis of supraventricular arrhythmia. For example, it has long been known that vagal stimulation or acetylcholine application to the heart can produce either atrial flutter or fibrillation, and can nonuniformly shorten atrial refractoriness periods, thus increasing the regional differences in atrial refractory period. In man, the onset of atrial fibrillation has a diurnal distribution with a statistically significant peak occurring at night. Further, spectral analysis of heart rate variability has suggested an increase in vagal drive immediately preceding the onset of atrial arrhythmia. Sympathetic stimulation or administration of catecholamines can also influence atrial electrophysiological properties. Isoproterenol shortens the atrial action potential and stimulation of sympathetic nerves shortens slightly atrial refractory period and can facilitate induction of atrial fibrillation. Furthermore, in man, attacks of atrial fibrillation have stellar ganglions produces localised shortening of the refractory period, increases the dispersion of refractoriness and increases the vulnerability to re-entrant arrhythmias.

The majority of the above observations have, however, been made with respect to atrial fibrillation and not atrial flutter. Indeed, very little is known of the influence of the autonomic nervous system tone on the electrophysiological characteristics of tissue within the circuit. In the only human study of autonomic system effects on atrial flutter, parasympathetic and sympathetic blockade with intravenous atropine and propranolol did not change atrial flutter cycle length either in the supine or upright position. Many of these patients were however on Class IA antiarrhythmics which in themselves have an anticholinergic effect. Furthermore, observations limited to cycle length although useful, do not describe the complex effects of the autonomic nervous system on the electrophysiological properties of tissue participating in the circuit. Only a study of the duration of the excitable gap can elucidate how the viability of the flutter circuit is modulated by autonomic effects. Indeed, properties such as atrial refractoriness and conduction velocity are influenced by autonomic input can be determined to measure the influence of autonomic nervous system on atrial arrhythmias.

Either adrenergic or vagal stimulation can favor the onset of atrial fibrillation through complex mechanisms of shortening of the atrial refractory period, affecting the heterogeneity of refractoriness, the conduction time and the resultant wavelength of the propagate of this atrial arrhythmias. Atrial fibrillation starts with a period of rapid ectopic activity that may be caused by discharge of an autonomic focus, or afterpotentials, particularly in the setting of an enhanced catecholamine state. Vagal tone stimulation initiates atrial fibrillation by hyperpolarization in the atrial tissues and fibres, an effect that does not favor either delayed afterdepolarization or pacemaker activity. Thus, it may facilitate the conditions for the reentry initiation because the duration of the P waves may actually become shorter than the time required to excite the whole atria. However, for those factors may also be the conditions for the perpetuation or the termination of those re-entrant atrial arrhythmnias. Clinical paroxysmal atrial arrhythmias suggesting a predominant vagal mechanism often display a pattern of atrial fibrillation with alternates of atrial flutter. In contrast, atrial fibrillation dependent of adrenergic activity is most likely related to ectopic automatic foci explained by their ECG appearance. The onset of atrial fibrillation that occurs in the setting of rest or digestive periods, and is preceded by a progressive heart rate decrease, could be related to a vagal activation mechanism. However, palpitations starting at exercise or stress are related to adrenergic mediation.

Class III Antiarrhythmic Drugs Mechanisms in Atrial Arrhythmias

Electrophysiological studies suggest that the mechanism of type I atrial flutter in humans and in canine models involves a macroreentrant circuit around an anatomically or anisotropically defined obstacle with either a partially or fully excitable gap. The excitable gap is one of the principle determinant of the continued circulation of the abnormal atrial impulse and in its presence an extrastimulus can preexcite the circuit and reset the tachycardia. Atrial fibrillation, a reentrant arrhythmia, is more likely to occur in the presence of an abnormally shortened atrial effective refractory period and increased dispersion of the effective refractory period. In addition, abnormally depressed conduction velocity and anatomic obstacles may play a role in the reentrant mechanism of atrial fibrillation. Experimental studies have suggested that prolongation of atrial wavelength and a reduction in effective refractory dispersion may be critical determinants of the efficacy of antiarrhythmic drugs in terminating and suppressing reentrant atrial arrhythmias. Both of these salutary electrophysiological effects are produced by class III antiarrhythmic drugs, such as sotalol. Despite their favourable electrophysiological profile, however, the class III drugs are not more effective than the class I drugs in suppressing atrial fibrillation in humans, with only 50% to 65% of patients in sinus rhythm after 6 months of therapy. In addition, the organ toxicity and potential life-threatening ventricular proarrhythmia associated with antiarrhythmic drugs further limit their use for treating atrial fibrillation. Because of the limited efficacy and potential adverse effects of antiarrhythmic drugs that modulate cardiac ion channels, new approaches to antiarrhythmic drug therapy must be developed. One possible approach is the modulation of membrane receptors that play a role in controlling normal cellular electrophysiology. Despite considerable advances in our understanding on the mechanism of this atrial arrhythmia, antiarrhythmic drug therapy to produce and maintain sinus rhythm is fraught with a variety of problems. These drugs are either incompletely effective, may have proarrhythmic properties, and also may increase mortality. Since some of the more dangerous proarrhythmic potential of antiarrhythmic drugs appears to be related to sodium channel blocking properties, there has been increased interest in class III drugs, which act by increasing action potential duration and refractoriness without blocking sodium channels. Sotalol is one such class III antiarrhythmic drugs which can exist in either the d- or l-isomer forms. Both isomers have equal class III activity but only the l-isomer possesses significant β-adrenoceptor blocking activity. d,l-Sotalol, the racemic, therefore has both class II and class III properties. It has been used both to terminate atrial arrhythmias and to prevent their recurrence following cardioversion. It blocks both the slow and rapid component of the delayed rectifier potassium current ($I_{ks}$ and $I_{kr}$) and thus increases the atrial action potential duration and the atrial effective refractory period. At high concentrations sotalol can also inhibit the background or inward rectifying $K^+$ ($I_{k1}$) and decreases the transient outward $K^+$ current ($I_{to}$). Administration of class III antiarrhythmic drugs has been reported to prevent and/or terminate atrial flutter an effect correlated with a shortening of the excitable gap and with prolongation of both the atrial flutter cycle length and the refractory period.

In a recent study in common human atrial flutter, edrophonium which blocks acetylcholinesterase activity had no significant effect on monophasic atrial action potential duration or atrial flutter cycle length. However, this study had some limitations. For example, the atrial monophasic action potentials were not obtained directly from the atrial flutter circuit. Furthermore, cholinesterase inhibition would not necessarily produce any change in action potential duration in the absence of simultaneous vagal activity. This invention also presents some limitations in the part of neurotransmitters infusion during the sustained atrial flutter: First, neurotransmitter infusion does not necessarily reproduce the synaptic cleft concentrations which occur with autonomic nervous system stimulation. Second, autonomic fibers may be non homogeneously distributed in the atrium and this distribution is different for the vagal and sympathetic systems. The latency time and duration of the physiological response are also different. This may contribute to a discrepancy between the effects of neurotransmitter infusion, which may produce a more homogeneous effect compared to the non homogeneous autonomic fiber stimulation. Finally, at the level of the neuroeffector junction and beyond, the effects of neurotransmitter infusion may differ from the effects of autonomic fiber stimulation. Parasympathetic and sympathetic system stimulation interact in four ways: (1) vagal stimulation inhibits the release of norepinephrine at sympathetic nerve terminals; (2) sympathetic stimulation releases neuropeptide Y, which in turn interferes with the actions of vagal stimulation, possibly by inhibiting the release of acetylcholine; (3) α-adrenergic stimulation with phenylephrine attenuates the bradycardia induced by direct vagus nerve stimulation; and (4) acetylcholine antagonizes the intracellular production of cyclic AMP by catecholamines. Therefore, the effects we observe with infusion of acetylcholine and norepinephrine likely do not reproduce quantitatively the effects of autonomic nerve activity. Nevertheless, these qualitative effects demonstrate an important modulation of atrial flutter excitable gap which can be clinically significant.

Methods

Atrial Flutter protocol: All experiments described were in accordance with institutional guidelines for animal experimentation. Fourteen mongrel dogs of either sex, weight 29–45 kg, were studied in the post-absorptive state. General anaesthesia was induced with sodium thiopental (25 mg/kg iv.) and maintained with chloralose (80 mg/kg iv. bolus supplemented by 20 mg/kg/hr maximum as needed). The dogs were intubated and ventilated (Harvard pump) with room air (10 breaths/min, tidal volume to achieve a maximum inspiratory pressure of 20 cm water) to maintain arterial pH 7.35–7.45 and $PaO_2$>80 mm Hg. Arterial and venous cannulae were inserted in the left femoral artery and vein by direct cut down for blood pressure monitoring and drug administration, respectively. An additional venous cannulae was inserted in the right femoral vein or in the right internal jugular vein for blood sampling. Muscular relaxation was then induced with gallamine triethiodide (Flaxedil 100) 3 mg/kg intravenously. A right thoracotomy was performed via the fourth or fifth intercostal space and the pericardium was incised to provide access to the vena cava and the right atrium. According to the procedure described by Frame et al., (1986) the tissue on a line extending from the superior to the inferior venae cavae was clamped, incised and sewn over. A second line, extending from the first two-thirds of the way toward the tip of the right atrial appendage and parallel to 1–2 cm above the atrioventricular groove, was similarly incised and sewn over. Five close (2–4 mm) bipolar epicardial silver electrodes (insulated except at the tip) for stimulating and/or recording were sewn around the base of the right atrium within 1 cm of the tricuspid annulus. Three were positioned on the anterior surface and two on the posterior surface (Derakhchan K, et al., 1994). An arterial cannula was inserted in the right coronary artery for neurotransmitter infusion.

Measurement of electrophysiologic parameters: A single lead (II) surface electrocardiogram, atrial electrograms from each of the 5 bipolar electrodes, and the femoral arterial pressure were monitored and recorded using a Nihon Kohden polygraph (Model RM6008). Data were also stored on a Hewlett-Packard tape recorder. Atrial flutter was induced by burst stimulation (20–30 beats at basic cycle length <100 ms). During stable flutter (cycle length variation <10 ms), a premature stimulus was introduced at the site located on this re-entry circuit after every 20th spontaneous beat (T) in 2 ms decrements beginning at coupling intervals equal to the cycle length of this atrial tachycardia. The interval between the last spontaneous beat and the response to the subsequent premature stimulus (Coupling Interval) as well as the interval between the response to the premature stimulus and the subscript ($T_1$) tachycardia beat (Return Cycle) were measured (peak-to-peak) at the electrode distal to the stimulating site (in the direction of wavefront propagation). Measurements were made at a paper speed of 100 mm/s using a Digimatic Caliper (Mitutoyo Corporation, Tokyo) which has a resolution of 0.01 mm. Graphs describing the relationship between the Return Cycle (ordinate) and the Coupling Interval (abscissa) of the premature beat or reset-response curves were constructed using points where ($T-T_1$)<2 ($T-T$) by more than 3 ms. The refractoriness duration of this re-entry circuit was defined as the shortest coupling interval which reset this tachycardia. This excitable gap is calculated from the tissue which conducted the premature beat. The excitable gap tissue was thus the interval between the refractoriness and the total cycle length of this atrial arrhythmia. A line was fitted to the ascending portion of the reset-response curve, using all points where the Return Cycle>flutter cycle length. The duration of the flat portion was then taken from the intersection of this line with a horizontal line drawn at the flutter cycle length on the ordinate. The excitable gap was characterized by the reset-response technique as previously described by Derakhchan et al. (1994). It assumes that the reentry circuit is located in the muscle ring immediately above the tricuspid valve as has been previously demonstrated (Frame et al., 1986) and that its location in the presence of drug is unchanged. Measures were performed under control conditions before and then during a constant infusion of norepinephrine into the right coronary artery (15 $\mu$g/min) and again during an acetylcholine infusion (2 $\mu$g/min) into the same artery after allowing 15 minutes for recovery from norepinephrine effects. Completion of the entire protocol on drug usually required one hour.

Statistical analysis: Data are presented as mean±standard deviation of the mean. When multiple measurements were performed in the same population, statistical comparisons were done using one way repeated-measures ANOVA with Bonferroni's correction for pairwise multiple comparisons. For all tests, a value of $P<0.05$ was considered to be statistically significant (details of statistics of each parameter are presented with the in the section: Description of Tables). Linear regression as described in Methods was determined to characterise the increasing portion of the reset-response curve.

Atrial Fibrillation protocol: Fourteen mongrel dogs weighing 19–30 kg were anaesthetised with morphine (2 mg/kg i.m.) and α-chloralose (100 mg/kg iv.) and ventilated by a respirator (NSH 34RH, Harvard Apparatus, South Natick, Mass.) via an endotracheal tube at a rate of 20–25 breaths per minute with a tidal volume obtained from a nomogram. Arterial blood gases were measured to ensure adequate oxygenation ($SaO_2>90\%$) and physiological pH (7.38–7.45). Body temperature was maintained with a homiothermic heating blanket. Catheters were inserted into the left femoral artery and both femoral veins and kept patent with heparinized saline solution (0.9%). A median sternotomy was performed, an incision was made into the pericardium extending from the cranial reflection to the ventricular apex, and a pericardial cradle was created. A pair of Teflon-coated stainless steel bipolar hook electrodes, one for stimulation and the other for recording atrial electrograms, were inserted intramural into the tip of the right atrial appendage. The position of the stimulating electrodes were located in the right atrial appendage (RA-1), left atrial appendage (LA-2), inferior vena cava (IVC-3), medial vena cava (MVC-4) and superior vena cava (SVC-5). A programmable stimulator and a stimulus isolator (Bloom Assoc., Flying Hills, Pa.) were used to deliver 4-msec square-wave pulses. Operational amplifiers (Bloom Association) and a Mingograp T-16, 16 channel recorder (Siemens-Elema Ltd., Toronto, Canada) were used to record the six standard surface electrocardiogram leads, arterial pressure, and stimulus artifacts. Electrocardiographic recordings were obtained at a paper speed of 200 mm/sec.

Activation Mapping: Five thin plastic sheets containing 112 bipolar electrodes with 1 mm interpolar and 6 mm interelectrode distances were sewn into position on atrial epicardial surface. One sheet was placed under the root of aorta to cover the anterior aspect of the atrial appendages and Bachman's bundle. Three sheets were sewn to the posterior aspects of the atrial appendages and to the free walls. The parietal pericardium was gently separated, and a fifth plaque was placed between the pulmonary arteries and veins. Each signal was filtered (30 to 400 Hz), digitized with 12-bit resolution and 1-KHz sampling rate, and transmitted into a microcomputer (model 286, Compaq Computer, Houston, Tex.). Software routines were used to amplify, display, and analyse each electrogram signal as well as to generate activation maps. Each electrogram was analyzed with computer-determined peak-amplitude criteria and was reviewed manually. The accuracy of activation time measurements was±0.5 ms. The data were downloaded on high-density diskettes for subsequent off-line analysis. Isochrone maps and activation times for each activation were recorded by the use of IBM ink jet printer. Hardware and software for the mapping system were obtained from Biomedical Instrumentation, Inc., Markham, Ontario.

Autonomic Nervous System model: Both cervical vagal trunks were isolated and decentralised approximately 3 cm proximal to the bifurcation of the common carotid artery, and bipolar hook electrodes (stainless steel insulated with Teflon except for the terminal 1–2 cm) were inserted via a 21-gauge needle into the middle of each nerve, with the electrode running within and parallel to vagal fibers for several centimetres. Both right and left stellar ganglions were found between the 2–3 intercostal level, and isolated and decentralised, then a bipolar hook electrodes were inserted via a 21-gauge needle into the dorsal and ventral ansae of each stellar ganglion. The left and right stellar ansae were stimulated with square-wave pulses of 2 ms duration, 10 Hz frequency and 6 volts. Adequate stellar stimulation was verified by an increase in arterial systolic/diastolic pressure (from the left side) and in heart rate (from the right side). Bilateral vagal nerve stimulation was delivered by an SD-9F stimulator (Grass Instruments, Inc., Quincy, Mass.), with a pulse width of 0.1 msec and a frequency of 1 Hz, with an amplitude of stimulation of 3–10 V, adjusted in each dog to two thirds of the threshold for the production of asystole under control conditions. At a constant basic cycle length of 200 ms, we have determined the effective refractory period duration and the conduction velocity at baseline, vagal and sympathetic denervation. Fifteen seconds after the initiation of vagal (1 Hz, 0.1 ms) and sympathetic stimulation (10 Hz, 2 ms), we started to determine the effective refractory period and conduction velocity duration. Atrial fibrillation initiations were determined by short burst (1–3 seconds) of atrial pacing at a cycle length of 60–100 ms and with a current amplitude of four times the diastolic threshold for atrial capture. Atrial fibrillation duration was determined by the mean of 10 atrial fibrillation episodes during baseline conditions, vagal denervation, vagal stimulation (1 Hz, 0.1 ms) during 3 minutes, sympathetic denervation, vagal stimulation (1 Hz, 0.1 ms) during 3 minutes, and on the combined vagal (1 Hz, 0.1 ms) and sympathetic (10 Hz, 2 ms) stimulation during 3 minutes. If the duration of any atrial fibrillation episode on vagal or sympathetic stimulation was >3 minutes, no further stimulation are required. Animals with atrial fibrillation duration episodes >3 minutes at baseline conditions are excluded from this study.

Results

Reversal of d-sotalol effects on the atrial flutter circuit compositions by autonomic nervous system neurotransmitters:

The characteristics of the atrial flutter circuit are detailed in Table 1 from 6 animals. Both norepinephrine and acetylcholine infusion significantly shortened the effective refractory period duration. However, only acetylcholine infusion significantly shortened the atrial flutter cycle length and the excitable gap duration. In the presence of pure class 3 antiarrhythmic drug, d-sotalol, both norepinephrine and acetylcholine significantly reversed the effects of d-sotalol on the atrial flutter cycle length and on the effective refractory period duration, but only acetylcholine infusion significantly reversed d-sotalol effects on the excitable gap duration.

Selective reversal of d,l-sotalol effects on the atrial flutter circuit compositions by the parasympathetic nervous system neurotransmitters:

The characteristics of the atrial flutter circuit are detailed in Table 2 from 7 animals. Acetylcholine infusion significantly decreased the effective refractory period duration and increased the excitable gap duration. In the presence of d,l-sotalol, a class 3 combined with anti-adrenergic effects, acetylcholine significantly reversed d,l-sotalol effects on the atrial flutter cycle length, on the effective refractory period and on the excitable gap duration.

Effects of autonomic nervous system on the atrial refractory period duration and dispersion, on the atrial conduction velocity and wavelength, and on the occurrence of atrial fibrillation after its initiation:

The results on the atrial fibrillation are detailed in Table 3 from 14 animals. Vagal denervation effects compared to the baseline conditions, significantly decreased the atrial fibrillation duration, the effective refractory period dispersion and the conduction velocity, and significantly increased the effective refractory period duration. Sympathetic denervation did not significantly changed the effects produced by the vagal denervation. However, sympathetic stimulation significantly reversed the effects of autonomic denervation on the atrial effective refractory period duration. In contrast, vagal stimulation before and after sympathetic denervation significantly reversed the effects of autonomic denervation on the atrial fibrillation duration, on the effective refractory period duration and dispersion and on the conduction velocity. Vagal stimulation effects compared from baseline conditions, significantly increased the atrial fibrillation duration and the conduction velocity, and significantly decreased the effective refractory period duration. The combined effects of sympathetic-parasympathetic stimulation compared to those of parasympathetic stimulation alone were significantly different only on the conduction velocity, however, these combined effects compared to those of sympathetic stimulation alone are significantly different on the effective refractory period duration and dispersion and on the conduction velocity.

DESCRIPTION OF TABLES AND STATISTICS:

Table 1

Reversal of d-sotalol Effects on the Atrial Flutter Circuit Compositions by Autonomic Nervous System Neurotransmitters Statistical analysis for atrial flutter cycle length (AF1CL), effective refractory period duration ($ERP_{dur}$) and excitable gap duration ($EG_{dur}$) are performed using one way repeated measures analysis of variance with Bonferroni's corrected method as shown in the following section for each parameter. Data for d-sotalol are not shown in this invention.

|  | Baseline | NE | ACh | d − S + NE | d − S + ACh |
| --- | --- | --- | --- | --- | --- |
| AF1CL | 132 ± 14 | 133 ± 12 | 123 ± 15*† | 131 ± 8† | 122 ± 9*† |
| $ERP_{dur}$ | 105 ± 9 | 86 ± 9*† | 65 ± 5*† | 98 ± 8† | 78 ± 8*† |
| $EG_{dur}$ | 26 ± 10 | 44 ± 4† | 48 ± 16*† | 30 ± 13 | 44 ± 12† |

Values are expressed as Mean ± SD (ms) from 6 animals.
*$P < 0.05$, significant difference from Baseline
†$P < 0.05$, significant difference from d-sotalol
Abbreviations: ACh: Acetylcholine, AF1CL: Atrial Flutter Cycle Length, d-S: d-Sotalol; $EG_{dur}$: Excitable Gap duration, $ERP_{dur}$: Effective Refractory Period duration, NE: Norepinephrine.

Table 2

Selective Reversal of d,l-sotalol Effects on the Atrial Flutter Circuit Compositions by Parasympathetic Neurotransmitters Statistical analysis for atrial flutter cycle length (AF1CL), effective refractory period duration ($ERP_{dur}$) and excitable gap duration ($EG_{dur}$) are performed using one way repeated measures analysis of variance with Bonferroni's corrected method as shown in the following section for each parameter. Data for d,l-sotalol are not shown in this invention.

|  | Baseline | NE | ACh | d,l − S + NE | d,l − S + ACh |
| --- | --- | --- | --- | --- | --- |
| AF1CL | 133 ± 15 | 132 ± 8† | 119 ± 17† | 144 ± 11* | 126 ± 7† |
| AERP | 105 ± 15 | 93 ± 7† | 64 ± 4*† | 121 ± 13 | 84 ± 14 |
| EG | 27 ± 4 | 39 ± 3 | 50 ± 16*† | 22 ± 12 | 42 ± 13*† |

Values are expressed as Mean ± SD (ms) from 7 animals.
*$P < 0.05$, significant difference from Baseline
†$P < 0.05$, significant difference from d,l-sotalol
Abbreviations: ACh: Acetylcholine, AF1CL: Atrial Flutter Cycle Length, d,l-S: d-Sotalol; $EG_{dur}$: Excitable Gap duration, $ERP_{dur}$: Effective Refractory Period duration, NE: Norepinephrine.

Table 3

Effects of Autonomic Nervous System on Atrial Effective Refractory Period Duration and Dispersion, Atrial Conduction Velocity and Wavelength, and on the Duration of Atrial Fibrillation Statistical analysis for atrial fibrillation duration ($AF_{dur}$), effective refractory period duration ($ERP_{dur}$), effective refractory period dispersion ($ERP_{disp}$), conduction velocity (CV) and wavelength (WL) are performed using one way repeated measures analysis of variance with Bonferroni's corrected method as shown in the following section for each parameter. As shown in the following statistics for each parameter, the number of animals used with each intervention are different according to the ability to realise the correct measurements.

|     | Bas | V-D | V1-S1 | (V + S)-D | S-S10 | V2-S1 | (V-S1) + (S-S10) |
|---|---|---|---|---|---|---|---|
| $AF_{dur}$ | 34 ± 31 | 16 ± 19* | 208 ± 21*† | 8 ± 10*†α | — | 209 ± 29*†β | 201 ± 22*†β |
| $ERP_{dur}$ | 99 ± 14 | 110 ± 13* | 89 ± 15*† | 113 ± 13*α | 102 ± 11†αβ | 90 ± 15*†βφ | 87 ± 12*†βφ |
| $ERP_{disp}$ | 16 ± 3 | 11 ± 3* | 19 ± 3† | 13 ± 4*α | 13 ± 4α | 17 ± 4†βφ | 17 ± 6†βφ |
| CV | 100 ± 16 | 90 ± 12* | 108 ± 15*† | 89 ± 10*α | 95 ± 14α | 111 ± 16*†βφ | 115 ± 15*†αβφ |
| WL | 10 ± 2 | 10 ± 1 | 9 ± 2 | 10 ± 2 | 10 ± 2 | 10 ± 2 | 10 ± 2 |

Values are expressed as Mean ± SD from 14 animals. (n = 13 for $ERP_{dur}$ and $ERP_{disp}$ on ($V_2$-S1) + (S-S10) conditions; n = 12 for CV and WL; n = 7 for $AF_{dur}$). $ERP_{dur}$ and $ERP_{disp}$ are expressed in ms, CV in cm/s, WL in cm, $AF_{dur}$ in s. $ERP_{dur}$, $ERP_{disp}$ and CV are determined at a basic cycle length (S1S1) of 200 ms, $AF_{dur}$ are determined from the mean duration of 10 AF after its initiations.
*$P < 0.05$, significant difference from baseline,
†$P < 0.05$, significant difference vs. V-D,
α$P < 0.05$, significant difference vs. V1-S1,
β$P < 0.05$, significant difference vs. (V + S)-D,
φ$P < 0.05$, significant difference vs. S-S10.
Abbreviations: $AF_{dur}$: Atrial Fibrillation duration, Bas: Baseline conditions, CV: Conduction Velocity, $ERP_{dur}$: Effective Refractory Period duration, $ERP_{disp}$: Effective Refractory Period dispersion, V-D: Vagal Denervation, V1-S1: Vagal Stimulation at 1 Hz before sympathetic denervation, (V + S)-D: Autonomic Nervous System (Vagal and Sympathetic) Denervation, S-S10: Sympathetic Stimulation at 10 Hz, $V_2$-S1: Vagal Stimulation at 1 Hz after right and left stellar ganglions denervation, (V-S1) + (S-S10): Vagal Stimulation at 1 Hz combined with Sympathetic Stimulation at 10 Hz, WL: Wavelength.

TABLE 1

Reversal of d-sotalol effects on the AF1CL by NE and ACh

|     | -1- Dog# | -2- Baseline | -3- NE | -4- ACh | -5- d-s | -6- d-S + NE | -7- d-S + ACh |
|---|---|---|---|---|---|---|---|
| 1 | 1.0000 | 106.0000 | 118.0000 | 96.0000 | data | 122.0000 | 110.0000 |
| 2 | 2.0000 | 131.0000 | 124.0000 | 120.0000 | data | 126.0000 | 120.0000 |
| 3 | 3.0000 | 140.0000 | 144.0000 | 130.0000 | data | 128.0000 | 126.0000 |
| 4 | 4.0000 | 134.0000 | 130.0000 | 128.0000 | data | 130.0000 | 122.0000 |
| 5 | 5.0000 | 136.0000 | 132.0000 | 122.0000 | data | 134.0000 | 118.0000 |
| 6 | 7.0000 | 146.0000 | 150.0000 | 140.0000 | data | 144.0000 | 136.0000 |
| 7 |  |  |  |  |  |  |  |
| 8 |  |  |  |  |  |  |  |
| 9Mean |  | 132.1667 | 133.0000 | 122.6667 | data | 130.6667 | 122.0000 |
| 10SD |  | 13.8335 | 12.0499 | 14.8414 | data | 7.6594 | 8.6718 |
| 11SEM |  | 5.6475 | 4.9193 | 6.0590 | data | 3.1269 | 3.5402 |

One Way Repeated Measures Analysis of Variance

| Normality Test: | Passed | (P = 0.0706) |  |  |  |
|---|---|---|---|---|---|
| Equal Variance Test: | Passed | (P = 0.6738) |  |  |  |
| Group | N | Missing | Mean | Std Dev | SEM |
| Baseline | 6 | 0 | 132.2 | 13.83 | 5.65 |
| NE | 6 | 0 | 133.0 | 12.05 | 4.92 |
| ACh | 6 | 0 | 122.7 | 14.84 | 6.06 |
| d-S | 6 | 0 | data | 12.32 | 5.03 |
| d-S + NE | 6 | 0 | 130.7 | 7.66 | 3.13 |
| d-S + ACh | 6 | 0 | 122.0 | 8.67 | 3.54 |

Power of performed test with alpha = 0.0500: 1.0000

| Source of Variance | DF | SS | MS | F | P |
|---|---|---|---|---|---|
| Between Subjects | 5 | 3678.0 | 735.6 |  |  |
| Between Treatments | 5 | 1452.0 | 290.4 | 13.6 | 0.00000188 |
| Residual | 25 | 535.0 | 21.4 |  |  |
| Total | 35 | 5665.0 |  |  |  |

The differences in the mean values among the treatment groups are greater than would be expected by chance; there is a statistically significant difference (P = 0.00000188). To isolate the group or groups that differ from the others use a multiple comparison procedure.
All Pairwise Multiple Comparison Procedures (Bonferroni's method):

| Comparison | Diff of Means | t | P < 0.05 |
|---|---|---|---|
| Baseline vs d-S + ACh | 10.167 | 3.807 | Yes |
| Baseline vs d-S + NE | 1.500 | 0.562 | No |
| Baseline vs ACh | 9.500 | 3.557 | Yes |
| Baseline vs NE | −0.833 | −0.312 | No |
| Baseline vs d-s | data | data | — |
| NE vs d-S + ACh | 11.000 | 4.119 | Yes |

TABLE 1-continued

| | | | |
|---|---|---|---|
| NE vs d-S + NE | 2.333 | 0.874 | No |
| NE vs d-S | −7.500 | −2.808 | No |
| NE vs ACh | 10.333 | 3.869 | Yes |
| ACh vs d-S + ACh | 0.667 | 0.250 | No |
| ACh vs d-S + NE | −8.000 | −2.995 | No |
| ACh vs d-S | −17.833 | −6.677 | Yes |
| d-S vs d-S + ACh | 18.500 | 6.927 | Yes |
| d-S vs d-S + NE | 9.833 | 3.682 | Yes |
| d-S + NE vs d-S + ACh | 8.667 | 3.245 | Yes |

Reversal of d-sotalol effects on the atrial ERP by NE and ACh

| | -1- Dog# | -2- Baseline | -3- NE | -4- ACh | -5- d-s | -6- d-S + NE | -7- d-S + ACh |
|---|---|---|---|---|---|---|---|
| 1 | 1.0000 | 90.0000 | 80.0000 | 62.0000 | data | 106.0000 | 80.0000 |
| 2 | 2.0000 | 102.0000 | 78.0000 | 64.0000 | data | 100.0000 | 84.0000 |
| 3 | 3.0000 | 118.0000 | — | 58.0000 | data | 102.0000 | 64.0000 |
| 4 | 4.0000 | 106.0000 | 86.0000 | 72.0000 | data | 100.0000 | 78.0000 |
| 5 | 5.0000 | 102.0000 | 88.0000 | 68.0000 | data | 84.0000 | 82.0000 |
| 6 | 7.0000 | 110.0000 | 100.0000 | — | data | — | — |
| 7 | | | | | | | |
| 8 | | | | | | | |
| 9 Mean | | 104.6667 | 86.4000 | 64.8000 | data | 98.4000 | 77.6000 |
| 10 SD | | 9.3524 | 8.6487 | 5.4037 | data | 8.4143 | 7.9246 |
| 11 SEM | | 3.8181 | 3.8678 | 2.4166 | data | 3.7630 | 3.5440 |

One Way Repeated Measures Analysis of Variance

Normality Test: Passed (P = 0.2769)
Equal Variance Test: Passed (P = 0.8519)

| Group | N | Missing | Mean | Std Dev | SEM |
|---|---|---|---|---|---|
| Baseline | 6 | 0 | 104.7 | 9.35 | 3.82 |
| NE | 6 | 1 | 86.4 | 8.65 | 3.87 |
| ACh | 6 | 1 | 64.8 | 5.40 | 2.42 |
| d-S | 6 | 0 | data | 7.16 | 2.92 |
| d-S + NE | 6 | 1 | 98.4 | 8.41 | 3.76 |
| d-S + ACh | 6 | 1 | 77.6 | 7.92 | 3.54 |

Power of performed test with alpha = 0.0500: 1.0000

| Source of Variance | DF | SS | MS | F | P |
|---|---|---|---|---|---|
| Between Subjects | 5 | 322.8 | 64.6 | | |
| Between Treatments | 5 | 9269.7 | 1853.9 | 29.5 | 0.00000000813 |
| Residual | 21 | 1321.0 | 62.9 | | |
| Total | 31 | 11735.5 | 378.6 | | |

The differences in the mean values among the treatment groups are greater than would be expected by chance; there is a statistically significant difference (P = 0.00000000813). To isolate the group or groups that differ from the others use a multiple comparison procedure.
Expected Mean Squares:

Approximate DF Residual = 21.0
E{MS(Subj)) = var(res) + 5.20 var(Subj)
E{MS(Treatment)) var(res) + var(Treatment)
E{MS(Residual)l var(res)
All Pairwise Multiple Comparison Procedures (Bonferroni's method)

| Comparison | Diff of Means | t | P < 0.05 |
|---|---|---|---|
| Baseline vs d-S + ACh | 25.68 | 5.27 | Yes |
| Baseline vs d-S + NE | 4.88 | 1.00 | No |
| Baseline vs d-S | data | data | — |
| Baseline vs ACh | 38.48 | 7.89 | Yes |
| Baseline vs NE | 18.17 | 3.75 | Yes |
| NE vs d-S + ACh | 7.51 | 1.45 | No |
| NE vs d-S + NE | −13.29 | −2.58 | No |
| NE vs d-S | −31.51 | −6.50 | Yes |
| NE vs ACh | 20.31 | 3.93 | Yes |
| ACh vs d-S + ACh | −12.80 | −2.55 | No |
| ACh vs d-S + NE | −33.60 | −6.70 | Yes |
| ACh vs d-S | −51.81 | −10.63 | Yes |
| d-S vs d-S + ACh | 39.01 | 8.00 | Yes |
| d-S vs d-S + NE | 18.21 | 3.73 | Yes |
| d-S + NE vs d-S + ACh | 20.80 | 4.15 | Yes |

TABLE 1-continued

Reversal of d-sotalol effects on the atrial EG by NE and Ach

|   | -1-<br>Dog# | -2-<br>Baseline | -3-<br>NE | -4-<br>ACh | -5-<br>d-s | -6-<br>d-S + NE | -7-<br>d-S + ACh |
|---|---|---|---|---|---|---|---|
| 1 | 1.0000 | 16.0000 | 38.0000 | 34.0000 | data | 16.0000 | 30.0000 |
| 2 | 2.0000 | 29.0000 | 46.0000 | 56.0000 | data | 26.0000 | 36.0000 |
| 3 | 3.0000 | 12.0000 | — | 72.0000 | data | 26.0000 | 62.0000 |
| 4 | 4.0000 | 21.0000 | 44.0000 | 42.0000 | data | 30.0000 | 44.0000 |
| 5 | 5.0000 | 34.0000 | 44.0000 | 34.0000 | data | 50.0000 | 36.0000 |
| 6 | 7.0000 | 36.0000 | 50.0000 | — | data | — | — |
| 7 | | | | | | | |
| 8 | | | | | | | |
| 9 Mean | | 25.8333 | 44.4000 | 47.6000 | data | 29.6000 | 41.6000 |
| 10 SD | | 9.7245 | 4.3359 | 16.3340 | data | 12.5220 | 12.4419 |
| 11 SEM | | 3.9700 | 1.9391 | 7.3048 | data | 5.6000 | 5.5642 |

One Way Repeated Measures Analysis of Variance

Normality Test:     Passed     (P = 0.2769)
Equal Variance Test: Passed    (P = 0.8519)

| Group | N | Missing | Mean | Std Dev | SEM |
|---|---|---|---|---|---|
| Baseline | 6 | 0 | 25.8 | 9.72 | 3.97 |
| NE | 6 | 1 | 44.4 | 4.34 | 1.94 |
| ACh | 6 | 1 | 47.6 | 16.33 | 7.30 |
| d-S | 6 | 0 | data | 8.80 | 3.59 |
| d-S + NE | 6 | 1 | 29.6 | 12.52 | 5.60 |
| d-S + ACh | 6 | 1 | 41.6 | 12.44 | 5.56 |

Power of performed test with alpha = 0.0500: 1.0000

| Source of Variance | DF | SS | MS | F | P |
|---|---|---|---|---|---|
| Between Subjects | 5 | 1177.9 | 235.6 | | |
| Between Treatments | 5 | 3368.9 | 673.8 | 6.83 | 0.000631 |
| Residual | 21 | 2071.3 | 98.6 | | |
| Total | 31 | 6283.9 | 202.7 | | |

The differences in the mean values among the treatment groups are greater than would be expected by chance; there is a statistically significant difference (P = 0.000631). To isolate the group or groups that differ from the others use a multiple comparison procedure.

Expected Mean Squares:

Approximate DF Residual = 21.0
E{MS(Subj)} = var(res) + 5.20 var(Subj)
E{MS(Treatment)} var(res) + var(Treatment)
E{MS(Residual)} var(res)

All Pairwise Multiple Comparison Procedures (Bonferroni's method)

| Comparison | Diff of Means | t | P < 0.05 |
|---|---|---|---|
| Baseline vs d-S + ACh | −17.87 | −2.927 | No |
| Baseline vs d-S + NE | −5.87 | −0.962 | No |
| Baseline vs d-S | data | data | — |
| Baseline vs ACh | −23.87 | −3.855 | Yes |
| Baseline vs NE | −19.23 | −3.167 | No |
| NE vs d-S + ACh | 1.35 | 0.210 | No |
| NE vs d-S + NE | 13.35 | 2.066 | No |
| NE vs d-S | 22.56 | 3.716 | Yes |
| NE vs ACh | −4.65 | −0.719 | No |
| ACh vs d-S + ACh | 6.00 | 0.955 | No |
| ACh vs d-S + NE | 18.00 | 2.866 | No |
| ACh vs d-S | 27.21 | 4.456 | Yes |
| d-S vs d-S + ACh | −21.21 | −3.473 | Yes |
| d-S vs d-S + NE | −9.21 | −1.508 | No |
| d-S + NE vs d-S + ACh | −12.00 | −1.910 | No |

TABLE 2

Selective reversal of d,1-sotalol effects on the AF1CL by ACh

| | -1-<br>Dog# | -2-<br>Baseline | -3-<br>NE | -4-<br>ACh | -5-<br>d,1-S | -6-<br>d,1-S + NE | -7-<br>d,1-S + ACh |
|---|---|---|---|---|---|---|---|
| 1 | 1.0000 | 118.0000 | 130.0000 | 112.0000 | data | 130.0000 | 124.0000 |
| 2 | 2.0000 | 124.0000 | — | 102.0000 | data | 145.0000 | 130.0000 |
| 3 | 3.0000 | 130.0000 | 121.0000 | 126.0000 | data | 144.0000 | 120.0000 |
| 4 | 4.0000 | 114.0000 | — | 100.0000 | data | 132.0000 | 116.0000 |
| 5 | 5.0000 | 150.0000 | — | — | — | — | 136.0000 |
| 6 | 6.0000 | 144.0000 | 140.0000 | 138.0000 | data | 154.0000 | 128.0000 |
| 7 | 7.0000 | 148.0000 | 136.0000 | 136.0000 | data | 158.0000 | 130.0000 |
| 8 | | | | | | | |
| 9 Mean | | 132.5714 | 131.7500 | 119.0000 | data | 143.8333 | 126.2857 |
| 10 SD | | 14.7745 | 8.2614 | 16.7212 | data | 11.2857 | 6.7753 |
| 11 SEM | | 5.5842 | 4.1307 | 6.8264 | data | 4.6074 | 2.5608 |

One Way Repeated Measures Analysis of Variance

Normality Test:     Passed     (P = 0.6219)
Equal Variance Test: Passed    (P = 0.1191)

| Group | N | missing | Mean | Std Dev | SEM |
|---|---|---|---|---|---|
| Baseline | 7 | 0 | 132.6 | 14.77 | 5.58 |
| NE | 7 | 3 | 131.8 | 8.26 | 4.13 |
| ACh | 7 | 1 | 119.0 | 16.72 | 6.83 |
| d,1-S | 7 | 1 | 143.0 | 13.19 | 5.39 |
| d,1-S + NE | 7 | 1 | 143.8 | 11.29 | 4.61 |
| d,1-S + ACh | 7 | 0 | 126.3 | 6.78 | 2.56 |

Power of performed test with alpha = 0.0500: 1.0000

| Source of Variance | DF | SS | MS | F | P |
|---|---|---|---|---|---|
| Between Subjects | 6 | 3715.4 | 619.2 | | |
| Between Treatments | 5 | 3080.4 | 616.1 | 15.1 | 0.000000965 |
| Residual | 24 | 979.3 | 40.8 | | |
| Total | 35 | 7492.6 | 214.1 | | |

The differences in the mean values among the treatment groups are greater than would be expected by chance; there is a statistically significant difference (P = 0.000000965). To isolate the group or groups that differ from the others use a multiple comparison procedure.

Expected Mean Squares:

Approximate DF Residual = 24.0
E{MS(Subj)} = var(res) + 5.00 var(Subj)
E{MS(Treatment)} var(res) + var(Treatment)
E{MS(Residual)} var(res)

All Pairwise Multiple Comparison Procedures (Bonferroni's method):

| Comparison | Diff of Means | t | P < 0.05 |
|---|---|---|---|
| Baseline vs d,1-S + ACh | 6.286 | 1.841 | No |
| Baseline vs d,1-S + NE | -13.524 | -3.734 | Yes |
| Baseline vs d,1-S | data | data | — |
| Baseline vs ACh | 11.310 | 3.123 | No |
| Baseline vs NE | 3.226 | 0.778 | No |
| NE vs d,1-S + ACh | 3.060 | 0.738 | No |
| NE vs d,1-S + NE | -16.750 | -3.983 | Yes |
| NE vs d,1-S | -15.917 | -3.785 | Yes |
| NE vs ACh | 8.083 | 1.922 | No |
| ACh vs d,1-S + ACh | -5.024 | -1.387 | No |
| ACh vs d,1-S + NE | -24.833 | -6.733 | Yes |
| ACh vs d,1-S | -24.000 | -6.507 | Yes |
| d,1-S vs d,1-S + ACh | 18.976 | 5.240 | Yes |
| d,1-S vs d,1-S + NE | -0.833 | -0.226 | No |
| d,1-S + NE vs d,1-S + ACh | 19.810 | 5.470 | Yes |

Selective reversal of d,1-sotalol effects on the atrial ERP b ACh

| | -1-<br>Dog# | -2-<br>Baseline | -3-<br>NE | -4-<br>ACh | -5-<br>d,1-S | -6-<br>d,1-S + NE | -7-<br>d,1-S + ACh |
|---|---|---|---|---|---|---|---|
| 1 | 1.0000 | 86.0000 | 88.0000 | 58.0000 | data | 100.0000 | 74.0000 |
| 2 | 2.0000 | 100.0000 | — | 62.0000 | data | 122.0000 | 80.0000 |
| 3 | 3.0000 | 104.0000 | 86.0000 | 64.0000 | data | 114.0000 | 66.0000 |
| 4 | 4.0000 | 88.0000 | — | 64.0000 | data | 134.0000 | 88.0000 |
| 5 | 5.0000 | 120.0000 | — | — | data | — | 92.0000 |
| 6 | 6.0000 | 122.0000 | 102.0000 | — | data | 132.0000 | 108.0000 |

TABLE 2-continued

| | | | | | | | |
|---|---|---|---|---|---|---|---|
| 7 | 7.0000 | 114.0000 | 96.0000 | 70.0000 | data | 124.0000 | 80.0000 |
| 8 | | | | | | | |
| 9Mean | | 104.8571 | 93.0000 | 63.6000 | data | 121.0000 | 84.0000 |
| 10SD | | 14.5537 | 7.3937 | 4.3359 | data | 12.5698 | 13.6137 |
| 11SEM | | 5.5008 | 3.6968 | 1.9391 | data | 5.1316 | 5.1455 |

One Way Repeated Measures Analysis of Variance

| | | | | | |
|---|---|---|---|---|---|
| Normality Test: | Passed | (P = 0.0692) | | | |
| Equal Variance Test: | Passed | (P = 0.8009) | | | |
| Group | N | Missing | Mean | Std Dev | SEM |
| Baseline | 7 | 0 | 104.9 | 14.55 | 5.50 |
| NE | 7 | 3 | 93.0 | 7.39 | 3.70 |
| ACh | 7 | 2 | 63.6 | 4.34 | 1.94 |
| d,1-S | 7 | 1 | data | 19.12 | 7.84 |
| d,1-S + NE | 7 | 1 | 121.0 | 12.57 | 5.13 |
| d,1-S + ACh | 7 | 0 | 84.0 | 13.61 | 5.15 |

Power of performed test with alpha = 0.0500: 1.0000

| Source of Variance | DF | SS | MS | F | P |
|---|---|---|---|---|---|
| Between Subjects | 6 | 3472.2 | 578.7 | | |
| Between Treatments | 5 | 13459.0 | 2691.8 | 34.7 | 0.000000000563 |
| Residual | 23 | 1785.8 | 77.6 | | |
| Total | 34 | 19839.5 | 583.5 | | |

The differences in the mean values among the treatment groups are greater than would be expected by chance; there is a statistically significant difference (P = 0.000000000563). To isolate the group or groups that differ from the others use a multiple comparison procedure.

Expected Mean Squares:

Approximate DF Residual = 23.0
E{MS(Subj)} = var(res) + 4.83 var(Subj)
E{MS(Treatment)} var(res) + var(Treatment)
E{MS(Residual)} var(res)

All Pairwise Multiple Comparison Procedures (Bonferroni's method)

| Comparison | Diff of Means | t | P < 0.05 |
|---|---|---|---|
| Baseline vs d,1-S + ACh | 20.86 | 4.428 | Yes |
| Baseline vs d,1-S + NE | −18.07 | −3.617 | Yes |
| Baseline vs d,1-S | data | data | — |
| Baseline vs ACh | 35.70 | 6.738 | Yes |
| Baseline vs NE | 10.55 | 1.844 | No |
| NE vs d,1-S + ACh | 10.31 | 1.801 | No |
| NE vs d,1-S + NE | −28.62 | −4.932 | Yes |
| NE vs d,1-S | −30.62 | −5.277 | Yes |
| NE vs ACh | 25.15 | 4.112 | Yes |
| ACh vs d,1-S + ACh | −14.85 | −2.802 | No |
| ACh vs d,1-S + NE | −53.78 | −9.986 | Yes |
| ACh vs d,1-S | −55.78 | −10.357 | Yes |
| d,1-S vs d,1-S + ACh | 40.93 | 8.193 | Yes |
| d,1-S vs d,1-S + NE | 2.00 | 0.393 | No |
| d,1-S + NE vs d,1-S + ACh | 38.93 | 7.792 | Yes |

Selective reversal of d,1-sotalol effects on the atrial EG by ACh

| -1-<br>Dog# | -2-<br>Baseline | -3-<br>NE | -4-<br>ACh | -5-<br>d,1-S | -6-<br>d,1-S + NE | -7-<br>d,1-S + ACh |
|---|---|---|---|---|---|---|
| 1 | 1.0000 | 32.0000 | 42.0000 | 54.0000 | data | 30.0000 | 50.0000 |
| 2 | 2.0000 | 24.0000 | — | 44.0000 | data | 23.0000 | 50.0000 |
| 3 | 3.0000 | 26.0000 | 35.0000 | 62.0000 | data | 30.0000 | 54.0000 |
| 4 | 4.0000 | 26.0000 | — | 26.0000 | data | 2.0000 | 28.0000 |
| 5 | 5.0000 | 30.0000 | — | — | — | — | 44.0000 |
| 6 | 6.0000 | 22.0000 | 38.0000 | — | data | 12.0000 | 20.0000 |
| 7 | 7.0000 | 30.0000 | 40.0000 | 66.0000 | data | 34.0000 | 50.0000 |
| 8 | | | | | | | |
| 9Mean | | 25.8333 | 38.7500 | 50.4000 | data | 21.8333 | 42.2857 |
| 10SD | | 9.7245 | 2.9861 | 16.0250 | data | 12.4325 | 13.0348 |
| 11SEM | | 3.9700 | 1.4930 | 7.1666 | data | 5.07555 | 4.9267 |

TABLE 2-continued

One Way Repeated Measures Analysis of Variance

| Normality Test: | Failed | (P = 0.0328) | | | |
|---|---|---|---|---|---|
| Equal Variance Test: | Passed | (P = 0.8347) | | | |
| Group | N | Missing | Mean | Std Dev | SEM |
| Baseline | 7 | 0 | 27.1 | 3.63 | 1.37 |
| NE | 7 | 3 | 38.8 | 2.99 | 1.49 |
| ACh | 7 | 2 | 50.4 | 16.02 | 7.17 |
| d,1-S | 7 | 1 | data | 16.59 | 6.77 |
| d,1-S + NE | 7 | 1 | 21.8 | 12.43 | 5.08 |
| d,1-S + ACh | 7 | 0 | 42.3 | 13.03 | 4.93 |

Power of performed test with alpha = 0.0500: 0.9996

| Source of Variance | DF | SS | MS | F | P |
|---|---|---|---|---|---|
| Between Subjects | 6 | 2655.8 | 442.6 | | |
| Between Treatments | 5 | 3733.0 | 746.6 | 10.4 | 0.0000253 |
| Residual | 23 | 1645.3 | 71.5 | | |
| Total | 34 | 8549.5 | 251.5 | | |

The differences in the mean values among the treatment groups are greater than would be expected by chance; there is a statistically significant difference (P = 0.0000253). To isolate the group or groups that differ from the others use a multiple comparison procedure.
Expected Mean Squares:

Approximate DF Residual = 23.0
E{MS(Subj)} = var(res) + 4.83 var(Subj)
E{MS(Treatment)} = var(res) + var(Treatment)
E{MS(Residual)} var(res)

All Pairwise Multiple Comparison Procedures (Bonferroni's method)

| Comparison | Diff of Means | t | P < 0.05 |
|---|---|---|---|
| Baseline vs d,1-S + ACh | −15.14 | −3.350 | Yes |
| Baseline vs d,1-S + NE | 4.93 | 1.028 | No |
| Baseline vs d,1-S | data | data | — |
| Baseline vs ACh | −21.89 | −4.305 | Yes |
| Baseline vs NE | −8.32 | −1.515 | No |
| NE vs d,1-S + ACh | −6.82 | −1.242 | No |
| NE vs d,1-S + NE | 13.25 | 2.379 | No |
| NE vs d,1-S | 15.08 | 2.708 | No |
| NE vs ACh | −13.57 | −2.312 | No |
| ACh vs d,1-S + ACh | 6.75 | 1.328 | No |
| ACh vs d,1-S + NE | 26.82 | 5.189 | Yes |
| ACh vs d,1-S | 28.66 | 5.544 | Yes |
| d,1-S vs d,1-S + ACh | −21.90 | −4.568 | Yes |
| d,1-S vs d,1-S + NE | −1.83 | −0.375 | No |
| d,1-S + NE vs d,1-S + ACh | −20.07 | −4.186 | Yes |

TABLE 3

Effects of Autonomic Nervous Syst. on Atrial Fibrillation duration

| -1-<br>Mean-10 AF | -2-<br>Bas | -3-<br>V-D | -4-<br>V1-S1 | -5-<br>(V + S)-D | -6-<br>S-S10 | -7-<br>V2-S1 | -8-<br>V-S1 + S-S10 |
|---|---|---|---|---|---|---|---|
| 1 Dog#1 | 22.0000 | 9.0000 | 204.0000 | 9.0000 | 14.0000 | 260.0000 | 194.0000 |
| 2 Dog#2 | 33.0000 | 13.0000 | 189.0000 | 17.0000 | 13.0000 | 238.0000 | 190.0000 |
| 3 Dog#5 | 97.0000 | 44.0000 | 238.0000 | 31.0000 | — | 230.0000 | 209.0000 |
| 4 Dog#10 | 63.0000 | 56.0000 | 230.0000 | 36.0000 | 12.0000 | 214.0000 | 184.0000 |
| 5 Dog#12 | 22.0000 | 9.0000 | 190.0000 | 15.0000 | — | 182.0000 | 188.0000 |
| 6 Dog#13 | 34.0000 | 5.0000 | 189.0000 | 43.0000 | — | 208.0000 | 248.0000 |
| 7 Dog#14 | 13.0000 | 4.0000 | 218.0000 | 9.0000 | — | 183.0000 | 194.0000 |
| 8 | | | | | | | |
| 9 | | | | | | | |
| 10 | | | | | | | |
| 11 | | | | | | | |
| 12 Mean | 40.5714 | 20.0000 | 208.2857 | 18.5714 | — | 216.4286 | 201.0000 |
| 13 SD | 29.5458 | 20.9921 | 20.5970 | 10.7060 | — | 28.6581 | 22.1736 |
| 14 SEM | 11.1673 | 7.9343 | 7.7849 | 4.0465 | — | 10.8317 | 8.3808 |

TABLE 3-continued

One Way Repeated Measures Analysis of Variance

Normality Test:   Failed   (P = 0.0192)
Test execution ended by user request, RM ANOVA on Ranks begun
Friedman Repeated Measures Analysis of Variance on Ranks

| Group | N | Missing | Median | 25% | 75% |
|---|---|---|---|---|---|
| Bas | 7 | 0 | 33.00 | 22.00 | 55.8 |
| V-D | 7 | 0 | 9.00 | 6.00 | 36.3 |
| V1-S1 | 7 | 0 | 204.00 | 189.25 | 227.0 |
| (V + S)-D | 7 | 0 | 15.00 | 10.00 | 27.5 |
| V2-S1 | 7 | 0 | 214.00 | 189.25 | 236.0 |
| V-S1 + S-S10 | 7 | 0 | 194.00 | 188.50 | 205.3 |
| Tested | 7 | 0 | | | |

Chi-square = 30.5 with 5 degrees of freedom. (P < 0.0001)
The differences in the median values among the treatment groups are greater than would be expected by chance; there is a statistically significant difference (P = 0.0000116)
To isolate the group or groups that differ from the others use a multiple comparison procedure.
All Pairwise Multiple Comparison procedures.(Student-Newman-Keuls Method):

| Comparison | Diff of Ranks | p | q | P < 0.05 |
|---|---|---|---|---|
| V1-S1 vs V-D | 27.50 | 6 | 5.56 | Yes |
| V1-S1 vs (V + S)-D | 25.50 | 5 | 6.10 | Yes |
| V1-S1 vs Bas | 16.00 | 4 | 4.68 | Yes |
| V1-S1 vs V-S1 + S-S10 | 4.00 | 3 | 1.51 | No |
| V1-S1 vs V2-S1 | 2.00 | 2 | 1.07 | Do Not Test |
| V2-S1 vs V-D | 25.50 | 5 | 6.10 | Yes |
| V2-S1 vs (V + S)-D | 23.50 | 4 | 6.88 | Yes |
| V2-S1 vs Bas | 14.00 | 3 | 5.29 | Yes |
| V2-S1 vs V-S1 + S-S10 | 2.00 | 2 | 1.07 | Do Not Test |
| V-S1 + S-S10 vs V-D | 23.50 | 4 | 6.88 | Yes |
| V-S1 + S-S10 vs (V + S)-D | 21.50 | 3 | 8.13 | Yes |
| V-S1 + S-S10 vs Bas | 12.00 | 2 | 6.41 | Yes |
| Bas vs V-D | 11.50 | 3 | 4.35 | Yes |
| Bas vs (V + S)-D | 9.50 | 2 | 5.08 | Yes |
| (V + S)-D vs V-D | 2.00 | 2 | 1.07 | No |

Effects of Autonomic Nervous Syst. on AF duration (10 initiations)

| -1-<br>Dog#1/Init# | -2-<br>Bas | -3-<br>V-D | -4-<br>V1-S1 | -5-<br>(V + S)-D | -6-<br>S-S10 | -7-<br>V2-S1 | -8-<br>V-S1 + S-S10 |
|---|---|---|---|---|---|---|---|
| 1#1 | 3.0000 | 1.0000 | 204.0000 | 3.0000 | 20.0000 | 260.0000 | 194.0000 |
| 2#2 | 2.0000 | 2.0000 | | 2.0000 | — | | |
| 3#3 | 1.0000 | 2.0000 | | — | — | | |
| 4#4 | 30.0000 | 4.0000 | | 10.0000 | — | | |
| 5#5 | 45.0000 | — | | 2.0000 | 14.0000 | | |
| 6#6 | 80.0000 | 5.0000 | | 4.0000 | — | | |
| 7#7 | 12.0000 | — | | — | 10.0000 | | |
| 8#8 | 14.0000 | 7.0000 | | 14.0000 | — | | |
| 9#9 | 25.0000 | 46.0000 | | 21.0000 | 10.0000 | | |
| 10#10 | 5.0000 | 2.0000 | | 17.0000 | — | | |
| 11 | | | | | | | |
| 12Mean | 21.7000 | 8.6250 | 204.0000 | 9.1250 | 13.5000 | 260.0000 | 194.0000 |
| 13SD | 24.9891 | 15.2310 | 0.0000 | 7.4917 | 4.7258 | 0.0000 | 0.0000 |
| 14SEM | 7.9023 | 5.3850 | 0.0000 | 2.6487 | 2.3629 | 0.0000 | 0.0000 |

| -9- | -10- | -11- | -12- | -13- | -14- | -15- | -16- |
|---|---|---|---|---|---|---|---|
| Dog#2 | | | | | | | |
| 1#1 | 45.0000 | 10.0000 | 189.0000 | — | 12,0000 | 238.0000 | 190.0000 |
| 2#2 | 9.0000 | 2.0000 | | 14.0000 | 24.0000 | | |
| 3#3 | 14.0000 | — | | 17.0000 | 20.0000 | | |
| 4#4 | 75.0000 | — | | 2.0000 | 10.0000 | | |
| 5#5 | 2.0000 | 3.0000 | | 4.0000 | 10.0000 | | |
| 6#6 | 10.0000 | 14.0000 | | — | 8.0000 | | |
| 7#7 | 0.0000 | 21.0000 | | 12.0000 | 5.0000 | | |
| 8#8 | 17.0000 | 40.0000 | | 22.0000 | — | | |
| 9#9 | 5.0000 | 12.0000 | | 10.0000 | — | | |
| 10#10 | 154.0000 | 5.0000 | | 53.0000 | — | | |
| 11 | | | | | | | |
| 12Mean | 33.1000 | 13.3750 | 189.0000 | 16.7500 | 12.7143 | 238.0000 | 190.0000 |

TABLE 3-continued

| | | | | | | | |
|---|---|---|---|---|---|---|---|
| 13SD | 48.4251 | 12.4664 | 0.0000 | 16.0245 | 6.7999 | 0.0000 | 0.0000 |
| 14SEM | 15.3134 | 4.4075 | 0.0000 | 5.6655 | 2.5701 | 0.0000 | 0.0000 |

| -17- | -18- | -19- | -20- | -21- | -22- | -23- | -24- |
|---|---|---|---|---|---|---|---|
| Dog#5 | | | | | | | |
| 1#1 | 108.0000 | 80.0000 | 238.0000 | — | — | 230.0000 | 209.0000 |
| 2#2 | 36.0000 | 45.0000 | | 24.0000 | — | | |
| 3#3 | 42.0000 | 65.0000 | | 104.0000 | — | | |
| 4#4 | 80.0000 | 40.0000 | | 23.0000 | — | | |
| 5#5 | 30.0000 | — | | — | — | | |
| 6#6 | 104.0000 | 24.0000 | | 5.0000 | — | | |
| 7#7 | 174.0000 | 74.0000 | | — | — | | |
| 8#8 | 160.0000 | 12.0000 | | 10.0000 | — | | |
| 9#9 | 170.0000 | — | | 17.0000 | — | | |
| 10#10 | 69.0000 | 12.0000 | | 33.0000 | | | |
| 11 | | | | | | | |
| 12Mean | 97.3000 | 44.0000 | 238.0000 | 30.8571 | — | 230.0000 | 209.0000 |
| 13SD | 55.4818 | 26.9974 | 0.0000 | 33.5630 | — | 0.0000 | 0.0000 |
| 14SEM | 17.5449 | 9.5450 | 0.0000 | 12.6856 | — | 0.0000 | 0.0000 |

| -25- | -26- | -27- | -28- | -29- | -30- | -31- | -32- |
|---|---|---|---|---|---|---|---|
| Dog#10 | | | | | | | |
| 1#1 | — | — | 230.0000 | 4.0000 | 14.0000 | 214.0000 | 184.0000 |
| 2#2 | 12.0000 | — | | 7.0000 | 12.0000 | | |
| 3#3 | 74.0000 | 18.0000 | | 14.0000 | — | | |
| 4#4 | 24.0000 | 100.0000 | | 82.0000 | — | | |
| 5#5 | 51.0000 | — | | 90.0000 | 12.0000 | | |
| 6#6 | 10.0000 | 45.0000 | | 23.0000 | — | | |
| 7#7 | 102.0000 | — | | 21.0000 | 10.0000 | | |
| 8#8 | 80.0000 | 60.0000 | | 11.0000 | — | | |
| 9#9 | 60.0000 | 44.0000 | | 2.0000 | — | | |
| 10#10 | 158.0000 | 69.0000 | | 105.0000 | — | | |
| 11 | | | | | | | |
| 12Mean | 63.4444 | 56.0000 | 230.0000 | 35.9000 | 12.0000 | 214.0000 | 184.0000 |
| 13SD | 47.4845 | 27.6767 | 0.0000 | 39.8844 | 1.6330 | 0.0000 | 0.0000 |
| 14SEM | 15.8282 | 11.2990 | 0.0000 | 12.6126 | 0.8165 | 0.0000 | 0.0000 |

| -33- | -34- | -35- | -36- | -37- | -38- | -39- | -40- |
|---|---|---|---|---|---|---|---|
| Dog#12 | | | | | | | |
| 1#1 | 2.0000 | 1.0000 | 160.0000 | 11.0000 | — | 182.0000 | 188.0000 |
| 2#2 | 5.0000 | 20.0000 | 220.0000 | 13.0000 | | | |
| 3#3 | 36.0000 | 3.0000 | | — | | | |
| 4#4 | 14.0000 | 8.0000 | | 12.0000 | | | |
| 5#5 | 18.0000 | 7.0000 | | 11.0000 | | | |
| 6#6 | 61.0000 | 5.0000 | | 24.0000 | | | |
| 7#7 | 23.0000 | 12.0000 | | 28.0000 | | | |
| 8#8 | 41.0000 | 23.0000 | | 26.0000 | | | |
| 9#9 | — | 5.0000 | | 2.0000 | | | |
| 10#10 | 2.0000 | 3.0000 | | 5.0000 | | | |
| 11 | | | | | | | |
| 12Mean | 22.4444 | 8.7000 | 190.0000 | 14.6667 | — | 182.0000 | 188.0000 |
| 13SD | 20.1439 | 7.4394 | 42.4264 | 9.2466 | — | 0.0000 | 0.0000 |
| 14SEM | 6.7146 | 2.3525 | 30.0000 | 3.0822 | — | 0.0000 | 0.0000 |

| -41- | -42- | -43- | -44- | -45- | -46- | -47- | -48- |
|---|---|---|---|---|---|---|---|
| dog#13 | | | | | | | |
| 1#1 | 34.0000 | 1.0000 | 189.0000 | 5.0000 | — | 208.0000 | 248.0000 |
| 2#2 | 32.0000 | 2.0000 | | 14.0000 | 22.0000 | | |
| 3#3 | 54.0000 | 4.0000 | | 24.0000 | — | | |
| 4#4 | 87.0000 | 2.0000 | | 32.0000 | — | | |
| 5#5 | 60.0000 | 1.0000 | | 11.0000 | — | | |
| 6#6 | 2.0000 | — | | 5.0000 | — | | |
| 7#7 | 45.0000 | — | | 8.0000 | — | | |
| 8#8 | 4.0000 | 8.0000 | | 12.0000 | — | | |
| 9#9 | 7.0000 | 14.0000 | | 2.0000 | — | | |
| 10#10 | 11.0000 | 6.0000 | | 14.0000 | | | |
| 11 | | | | | | | |
| 12Mean | 33.6000 | 4.7500 | 189.0000 | 12.7000 | 22.0000 | 208.0000 | 248.0000 |
| 13SD | 28.2654 | 4.4960 | 0.0000 | 9.2021 | 0.0000 | 0.0000 | 0.0000 |
| 14SEM | 8.9383 | 1.5896 | 0.0000 | 2.9099 | 0.0000 | 0.0000 | 0.0000 |

TABLE 3-continued

| -49- | -50- | -51- | -52- | -53- | -54- | -55- | -56- |
|---|---|---|---|---|---|---|---|
| dog#13 | | | | | | | |
| 1#1 | 18.0000 | 2.0000 | 218.0000 | 14.0000 | — | 183.0000 | 194.0000 |
| 2#2 | 21.0000 | 4.0000 | | 28.0000 | — | | |
| 3#3 | — | 1.0000 | | 2.0000 | — | | |
| 4#4 | — | 2.0000 | | — | — | | |
| 5#5 | 18.0000 | 4.0000 | | — | — | | |
| 6#6 | 14.0000 | 3.0000 | | — | — | | |
| 7#7 | — | 2.0000 | | 3.0000 | — | | |
| 8#8 | 5.0000 | 5.0000 | | 6.0000 | — | | |
| 9#9 | 10.0000 | 15.0000 | | 8.0000 | — | | |
| 10#10 | 3.0000 | 2.0000 | | 5.0000 | | | |
| 11 | | | | | | | |
| 12Mean | 12.7143 | 4.0000 | 218.0000 | 9.4286 | — | 183.0000 | 194.0000 |
| 13SD | 6.9213 | 4.0552 | 0.0000 | 9.0895 | — | 0.0000 | 0.0000 |
| 14SEM | 2.6160 | 1.2824 | 0.0000 | 3.4355 | — | 0.0000 | 0.0000 |

Effects of Autonomic Nervous System on atrial ERP duration

| -1- Dogs # | -2- Bas | -3- V-D | -4- V1-S1 | -5- (V + S)-D | -6- S-S10 | -7- V2-S1 | -8- V-S1 + S-S10 |
|---|---|---|---|---|---|---|---|
| 1 | 1.0000 | 104.0000 | 118.0000 | 94.0000 | 122.0000 | 102.0000 | 100.0000 | 92.0000 |
| 2 | 2.0000 | 104.0000 | 108.0000 | 98.0000 | 112.0000 | 108.0000 | 102.0000 | 96.0000 |
| 3 | 3.0000 | 85.0000 | 93.0000 | 73.0000 | 98.0000 | 88.0000 | 78.0000 | 75.0000 |
| 4 | 4.0000 | 120.0000 | 125.0000 | 105.0000 | 120.0000 | 113.0000 | 105.0000 | 100.0000 |
| 5 | 5.0000 | 124.0000 | 130.0000 | 118.0000 | 134.0000 | 120.0000 | 120.0000 | 108.0000 |
| 6 | 6.0000 | 93.0000 | 117.0000 | 80.0000 | 130.0000 | 93.0000 | 83.0000 | |
| 7 | 7.0000 | 88.0000 | 108.0000 | 78.0000 | 104.0000 | 94.0000 | 76.0000 | 76.0000 |
| 8 | 8.0000 | 90.0000 | 100.0000 | 76.0000 | 106.0000 | 94.0000 | 78.0000 | 76.0000 |
| 9 | 9.0000 | 84.0000 | 100.0000 | 76.0000 | 102.0000 | 96.0000 | 74.0000 | 76.0000 |
| 10 | 10.0000 | 110.0000 | 115.0000 | 90.0000 | 110.0000 | 110.0000 | 90.0000 | 85.0000 |
| 11 | 11.0000 | 98.0000 | 108.0000 | 86.0000 | 110.0000 | 102.0000 | 92.0000 | 82.0000 |
| 12 | 12.0000 | 104.0000 | 112.0000 | 96.0000 | 116.0000 | 108.0000 | 90.0000 | 90.0000 |
| 13 | 13.0000 | 76.0000 | 82.0000 | 66.0000 | 88.0000 | 82.0000 | 66.0000 | 70.0000 |
| 14 | 14.0000 | 112.0000 | 120.0000 | 104.0000 | 124.0000 | 114.0000 | 102.0000 | 100.0000 |
| 15 | | | | | | | | |
| 16Mean | | 99.4286 | 109.7143 | 88.5714 | 112.5714 | 101.7143 | 89.7143 | 86.6154 |
| 17SD | | 14.1895 | 12.8628 | 14.7007 | 12.7322 | 10.9715 | 14.8864 | 11.9620 |
| 18SEM | | 3.7923 | 3.4377 | 3.9289 | 3.4028 | 2.9323 | 3.9786 | 3.3177 |

One Way Repeated Measures Analysis of Variance

| Normality Test: | Failed | (P = 0.0181) | | | |
|---|---|---|---|---|---|
| Equal Variance Test: | Passed | (P = 0.8712) | | | |
| Group | N | Missing | Mean | Std Dev | SEM |
| Bas | 14 | 0 | 99.4 | 14.2 | 3.79 |
| V-D | 14 | 0 | 109.7 | 12.9 | 3.44 |
| V1-S1 | 14 | 0 | 88.6 | 14.7 | 3.93 |
| (V + S)-D | 14 | 0 | 112.6 | 12.7 | 3.40 |
| S-S10 | 14 | 0 | 101.7 | 11.0 | 2.93 |
| V2-S1 | 14 | 0 | 89.7 | 14.9 | 3.98 |
| V-S1) + (S-S10 | 14 | 1 | 86.6 | 12.0 | 3.32 |

Power of performed test with alpha 0.0500: 1.0000

| Source of Variance | DF | SS | MS | F | P |
|---|---|---|---|---|---|
| Between Subjects | 13 | 14275.0 | 1098.1 | | |
| Between Treatments | 6 | 8987.0 | 1497.8 | 73.3 | 8.49E-030 |
| Residual | 77 | 1572.9 | 20.4 | | |
| Total | 96 | 24534.0 | 258.7 | | |

The differences in the mean values among the treatment groups are greater than would be expected by chance; there is a statistically significant difference (P = 8.49E-030). To isolate the group or groups that differ from the others use a multiple comparison procedure.

Expected Mean Squares:

Approximate DF Residual = 77.0
$E\{MS(Subj)\}$ = var(res) + 6.92 var(Subj)
$E\{MS(Treatment)\}$ = var(res) + var(Treatment)
$E\{MS(Residual)\}$ = var(res)

TABLE 3-continued

All Pairwise Multiple Comparison Procedures (Bonferroni's method):

| Comparison | Diff of Means | t | P < 0.05 |
|---|---|---|---|
| Bas vs V-S1) + (S-S10 | 12.89 | 7.380 | Yes |
| Bas vs V2-S1 | 9.71 | 5.687 | Yes |
| Bas vs S-S10 | −2.29 | −1.338 | No |
| Bas vs (V + S)-D | 13.14 | −7.694 | Yes |
| Bas vs V1-S1 | 10.86 | 6.356 | Yes |
| Bas vs V-D | −10.29 | −6.021 | Yes |
| V-D vs V-S1) + (S-S10 | 23.17 | 13.270 | Yes |
| V-D vs V2-S1 | 20.00 | 11.708 | Yes |
| V-D vs S-S10 | 8.00 | 4.683 | Yes |
| V-D vs (V + S)-D | −2.86 | −1.673 | No |
| V-D vs V1-S1 | 21.14 | 12.377 | Yes |
| V1-S1 vs V-S1) + (S-S10 | 2.03 | 1.162 | No |
| V1-S1 vs V2-S1 | −1.14 | −0.669 | No |
| V1-S1 vs S-S10 | −13.14 | −7.694 | Yes |
| V1-S1 vs (V + S)-D | −24.00 | −14.049 | Yes |
| (V + S)-D vs V-S1) + (S-S10 | 26.03 | 14.907 | Yes |
| (V + S)-D vs V2-S1 | 22.86 | 13.380 | Yes |
| (V + S)-D vs S-S10 | 10.86 | 6.356 | Yes |
| S-S10 vs V-S1) + (S-S10 | 15.17 | 8.689 | Yes |
| S-S10 vs V2-S1 | 12.00 | 7.025 | Yes |
| V2-S1 vs V-S1) + (S-S10 | 3.17 | 1.817 | No |

Effects of Autonomic Nervous System on atrial ERP dispersion

| | -1- Dogs # | -2- Bas | -3- V-D | -4- V1-S1 | -5- (V + S)-D | -6- S-S10 | -7- V2-S1 | -8- V-S1 + S-S10 |
|---|---|---|---|---|---|---|---|---|
| 1 | 1.0000 | 18.0000 | 11.0000 | 19.0000 | 8.0000 | 13.0000 | 20.0000 | 28.0000 |
| 2 | 2.0000 | 21.0000 | 18.0000 | 24.0000 | 16.0000 | 16.0000 | 23.0000 | 21.0000 |
| 3 | 3.0000 | 13.0000 | 10.0000 | 17.0000 | 13.0000 | 13.0000 | 15.0000 | 19.0000 |
| 4 | 4.0000 | 18.0000 | 13.0000 | 21.0000 | 18.0000 | 15.0000 | 21.0000 | 16.0000 |
| 5 | 5.0000 | 21.0000 | 14.0000 | 16.0000 | 15.0000 | 20.0000 | 16.0000 | 16.0000 |
| 6 | 6.0000 | 21.0000 | 15.0000 | 26.0000 | 17.0000 | 21.0000 | 21.0000 | |
| 7 | 7.0000 | 15.0000 | 8.0000 | 16.0000 | 11.0000 | 15.0000 | 18.0000 | 13.0000 |
| 8 | 8.0000 | 16.0000 | 10.0000 | 15.0000 | 9.0000 | 11.0000 | 11.0000 | 13.0000 |
| 9 | 9.0000 | 11.0000 | 7.0000 | 18.0000 | 15.0000 | 9.0000 | 15.0000 | 19.0000 |
| 10 | 10.0000 | 14.0000 | 7.0000 | 14.0000 | 14.0000 | 14.0000 | 14.0000 | 7.0000 |
| 11 | 11.0000 | 18.0000 | 13.0000 | 18.0000 | 7.0000 | 8.0000 | 22.0000 | 23.0000 |
| 12 | 12.0000 | 15.0000 | 11.0000 | 18.0000 | 17.0000 | 8.0000 | 16.0000 | 14.0000 |
| 13 | 13.0000 | 11.0000 | 8.0000 | 17.0000 | 8.0000 | 8.0000 | 11.0000 | 10.0000 |
| 14 | 14.0000 | 18.0000 | 12.0000 | 21.0000 | 9.0000 | 9.0000 | 18.0000 | 16.0000 |
| 15 | | | | | | | | |
| 16Mean | | 16.4286 | 11.2143 | 18.5714 | 12.6429 | 12.8571 | 17.2143 | 16.5385 |
| 17SD | | 3.4354 | 3.2148 | 3.3904 | 3.8751 | 4.3120 | 3.8666 | 5.5620 |
| 18SEM | | 0.9182 | 0.8592 | 0.9061 | 1.0357 | 1.1524 | 1.0334 | 1.5426 |

One Way Repeated Measures Analysis of Variance

Normality Test: Passed (P = 0.0589)
Equal Variance Test: Failed (P = 0.0181)

| Group | N | Missing | Mean Std Dev | Std Dev | SEM |
|---|---|---|---|---|---|
| Bas | 14 | 0 | 16.4 | 3.44 | 0.918 |
| V-D | 14 | 0 | 11.2 | 3.21 | 0.859 |
| Vl-S1 | 14 | 0 | 18.6 | 3.39 | 0.906 |
| (V + S)-D | 14 | 0 | 12.6 | 3.88 | 1.036 |
| S-S10 | 14 | 0 | 12.9 | 4.31 | 1.152 |
| V2-S1 | 14 | 0 | 17.2 | 3.87 | 1.033 |
| V-S1) + (S-S10 | 14 | 1 | 16.5 | 5.56 | 1.543 |

Power of performed test with alpha 0.0500: 1.0000

| Source of Variance | DF | SS | MS | F | P |
|---|---|---|---|---|---|
| Between Subjects | 13 | 735.2 | 56.55 | | |
| Between Treatments | 6 | 666.3 | 111.05 | 12.1 | 0.00000000148 |
| Residual | 77 | 704.5 | 9.15 | | |
| Total | 96 | 2088.7 | 21.76 | | |

The differences in the mean values among the treatment groups are greater than would be expected by chance; there is a statistically significant difference (P = 0.00000000148). To isolate the group or groups that differ from the others use a multiple comparison procedure.

TABLE 3-continued

Expected Mean Squares:

Approximate DF--Residual = 77.0  
E{MS(Subj)} = var(res) + 6.92 var(Subj)  
E{MS(Treatment)} = var(res) + var(Treatment)  
E{MS(Residual)} = var(res)

All Pairwise Multiple Comparison Procedures (Bonferroni's method):

| Comparison | Diff of Means | t | P < 0.05 |
|---|---|---|---|
| Bas vs V-S1) + (S-S10 | −0.521 | −0.446 | No |
| Bas vs V2-S1 | −0.786 | −0.687 | No |
| Bas vs S-S10 | 3.571 | 3.124 | No |
| Bas vs (V + S)-D | 3.786 | 3.311 | Yes |
| Bas vs V1-S1 | −2.143 | −1.874 | No |
| Bas vs V-D | 5.214 | 4.561 | Yes |
| V-D vs V-S1) + (S-S10 | −5.735 | −4.908 | Yes |
| V-D vs V2-S1 | −6.000 | −5.248 | Yes |
| V-D vs S-S10 | −1.643 | −1.437 | No |
| V-D vs (V + S)-D | −1.429 | −1.250 | No |
| V-D vs V1-S1 | −7.357 | −6.435 | Yes |
| V1-S1 vs V-S1) + (S-S10 | 1.622 | 1.388 | No |
| V1-S1 vs V2-S1 | 1.357 | 1.187 | No |
| V1-S1 vs S-S10 | 5.714 | 4.998 | Yes |
| V1-S1 vs (V + S)-D | 5.929 | 5.186 | Yes |
| (V + S)-D vs V-S1) + (S-S10 | −4.307 | −3.685 | Yes |
| (V + S)-D vs V2-S1 | −4.571 | −3.998 | Yes |
| (V + S)-D vs S-S10 | −0.214 | −0.187 | No |
| S-S10 vs V-S1) + (S-S10 | −4.092 | −3.502 | Yes |
| S-S10 vs V2-S1 | −4.357 | −3.811 | Yes |
| V2-S1 vs V-S1) + (S-S10 | 0.265 | 0.226 | No |

Effective Refractory Period (ERP) dispersion (disp) (5 sites, dog1)

| -1- ERPdisp | -2- Bas | -3- V-D | -4- V1-S1 | -5- (V + )S-D | -6- S-S10 | -7- V2-S1 | -8- V-S1 + S-S10 |
|---|---|---|---|---|---|---|---|
| 1RA-app | 130.0000 | 130.0000 | 120.0000 | 130.0000 | 120.0000 | 120.0000 | 120.0000 |
| 2LA-app | 100.0000 | 120.0000 | 100.0000 | 130.0000 | 100.0000 | 120.0000 | 120.0000 |
| 3RA-IVC | 110.0000 | 120.0000 | 100.0000 | 120.0000 | 110.0000 | 100.0000 | 90.0000 |
| 4RA-MVC | 100.0000 | 120.0000 | 80.0000 | 110.0000 | 90.0000 | 80.0000 | 70.0000 |
| 5RA-SVC | 80.0000 | 100.0000 | 70.0000 | 120.0000 | 90.0000 | 80.0000 | 60.0000 |
| 6 | | | | | | | |
| 7Mean | 104.0000 | 118.0000 | 94.0000 | 122.0000 | 102.0000 | 100.0000 | 92.0000 |
| 8SD | 18.1659 | 10.9545 | 19.4936 | 8.3666 | 13.0384 | 20.0000 | 27.7489 |
| 9SEM | 8.1240 | 4.8990 | 8.7178 | 3.7417 | 5.8310 | 8.9443 | 12.4097 |

Effective Refractory Period (ERP) dispersion (disp) (5 sites, dog2)

| -1- ERPdisp | -2- Bas | -3- V-D | -4- V1-S1 | -5- (V + )S-D | -6- S-S10 | -7- V2-S1 | -8- V-S1 + S-S10 |
|---|---|---|---|---|---|---|---|
| 1RA-app | 120.0000 | 120.0000 | 110.0000 | 120.0000 | 120.0000 | 110.0000 | 110.0000 |
| 2LA-app | 130.0000 | 130.0000 | 130.0000 | 130.0000 | 120.0000 | 130.0000 | 120.0000 |
| 3RA-IVC | 100.0000 | 110.0000 | 100.0000 | 120.0000 | 120.0000 | 110.0000 | 100.0000 |
| 4RA-MVC | 80.0000 | 90.0000 | 70.0000 | 100.0000 | 90.0000 | 70.0000 | 70.0000 |
| 5RA-SVC | 90.0000 | 90.0000 | 80.0000 | 90.0000 | 90.0000 | 90.0000 | 80.0000 |
| 6 | | | | | | | |
| 7Mean | 104.0000 | 108.0000 | 98.0000 | 112.0000 | 108.0000 | 102.0000 | 96.0000 |
| 8SD | 210.7364 | 17.8885 | 23.8747 | 16.4317 | 16.4317 | 22.8035 | 20.7364 |
| 9SEM | 9.2736 | 8.0000 | 10.6771 | 7.3485 | 7.3485 | 10.1980 | 9.2736 |

Effective Refractory Period (ERP) dispersion (disp) (4 sites, dog3)

| -1- ERPdisp | -2- Bas | -3- V-D | -4- V1-S1 | -5- (V + )S-D | -6- S-S10 | -7- V2-S1 | -8- V-S1 + S-S10 |
|---|---|---|---|---|---|---|---|
| 1RA-app | 100.0000 | 100.0000 | 90.0000 | 110.0000 | 100.0000 | 90.0000 | 90.0000 |
| 2LA-app | | | | | | | |
| 3RA-IVC | 90.0000 | 100.0000 | 80.0000 | 100.0000 | 90.0000 | 90.0000 | 90.0000 |
| 4RA-MVC | 80.0000 | 90.0000 | 70.0000 | 100.0000 | 90.0000 | 70.0000 | 70.0000 |
| 5RA-SVC | 70.0000 | 80.0000 | 50.0000 | 80.0000 | 70.0000 | 60.0000 | 50.0000 |
| 6 | | | | | | | |
| 7Mean | 85.0000 | 92.5000 | 72.5000 | 97.5000 | 87.5000 | 77.5000 | 75.0000 |
| 8SD | 12.9099 | 9.5743 | 17.0783 | 12.5831 | 12.5831 | 15.0000 | 19.1485 |
| 9SEM | 6.4550 | 4.7871 | 8.5391 | 6.2915 | 6.2915 | 7.5000 | 9.5743 |

TABLE 3-continued

Effective Refractory Period (ERP) dispersion (disp) (4 sites, dog4)

| -1- ERPdisp | -2- Bas | -3- V-D | -4- V1-S1 | -5- (V + )S-D | -6- S-S10 | -7- V2-S1 | -8- V-S1 + S-S10 |
|---|---|---|---|---|---|---|---|
| 1RA-app | 130.0000 | 130.0000 | 110.0000 | 130.0000 | 130.0000 | 110.0000 | 100.0000 |
| 2LA-app | 140.0000 | 140.0000 | 130.0000 | 140.0000 | 120.0000 | 130.0000 | 120.0000 |
| 3RA-IVC | 100.0000 | 110.0000 | 100.0000 | 100.0000 | 100.0000 | 100.0000 | 100.0000 |
| 4RA-MVC | 110.0000 | 120.0000 | 80.0000 | 110.0000 | 100.0000 | 80.0000 | 80.0000 |
| 5RA-SVC | | | | | | | |
| 6 | | | | | | | |
| 7Mean | 120.0000 | 125.0000 | 105.0000 | 120.0000 | 112.5000 | 105.0000 | 100.0000 |
| 8SD | 18.2574 | 12.9099 | 20.8167 | 18.2574 | 15.0000 | 20.8167 | 16.3299 |
| 9SEM | 9.1287 | 6.4550 | 10.4083 | 9.1287 | 7.5000 | 10.4083 | 8.1650 |

Effective Refractory Period (ERP) dispersion (disp) (5 sites, dog5)

| -1- ERPdisp | -2- Bas | -3- V-D | -4- V1-S1 | -5- (V + )S-D | -6- S-S10 | -7- V2-S1 | -8- V-S1 + S-S10 |
|---|---|---|---|---|---|---|---|
| 1RA-app | 140.0000 | 140.0000 | 130.0000 | 150.0000 | 140.0000 | 130.0000 | 120.0000 |
| 2LA-app | 150.0000 | 150.0000 | 140.0000 | 150.0000 | 140.0000 | 140.0000 | 130.0000 |
| 3RA-IVC | 120.0000 | 120.0000 | 110.0000 | 130.0000 | 120.0000 | 110.0000 | 100.0000 |
| 4RA-MVC | 100.0000 | 120.0000 | 110.0000 | 120.0000 | 100.0000 | 120.0000 | 100.0000 |
| 5RA-SVC | 110.0000 | 120.0000 | 100.0000 | 120.0000 | 100.0000 | 100.0000 | 90.0000 |
| 6 | | | | | | | |
| 7Mean | 124.0000 | 130.0000 | 118.0000 | 134.0000 | 120.0000 | 120.0000 | 108.0000 |
| 8SD | 20.7364 | 14.1421 | 16.4317 | 15.1658 | 20.0000 | 15.8114 | 16.4317 |
| 9SEM | 9.2736 | 6.3246 | 7.3485 | 6.7823 | 8.9443 | 7.0711 | 7.3485 |

Effective Refractory Period (ERP) dispersion (disp) (3 sites, dog6)

| -1- ERPdisp | -2- Bas | -3- V-D | -4- V1-S1 | -5- (V + )S-D | -6- S-S10 | -7- V2-S1 | -8- V-S1 + S-S10 |
|---|---|---|---|---|---|---|---|
| 1RA-app | 110.0000 | 120.0000 | 100.0000 | 140.0000 | 110.0000 | 100.0000 | — |
| 2LA-app | 100.0000 | 130.0000 | 90.0000 | 140.0000 | 100.0000 | 90.0000 | — |
| 3RA-IVC | 70.0000 | 100.0000 | 50.0000 | 110.0000 | 70.0000 | 60.0000 | — |
| 4RA-MVC | | | | | | | |
| 5RA-SVC | | | | | | | |
| 6 | | | | | | | |
| 7Mean | 93.3333 | 116.6667 | 80.0000 | 130.0000 | 93.3333 | 83.3333 | — |
| 8SD | 20.8167 | 15.2753 | 26.4575 | 17.3205 | 20.8167 | 20.8167 | — |
| 9SEM | 12.0185 | 8.8192 | 15.2753 | 10.0000 | 12.0185 | 12.0185 | — |

Effective Refractory Period (ERP) dispersion (disp) (5 sites, dog7)

| -1- ERPdisp | -2- Bas | -3- V-D | -4- V1-S1 | -5- (V + )S-D | -6- S-S10 | -7- V2-S1 | -8- V-S1 + S-S10 |
|---|---|---|---|---|---|---|---|
| 1RA-app | 110.0000 | 120.0000 | 100.0000 | 120.0000 | 110.0000 | 100.0000 | 90.0000 |
| 2LA-app | 90.0000 | 110.0000 | 90.0000 | 100.0000 | 110.0000 | 90.0000 | 90.0000 |
| 3RA-IVC | 70.0000 | 100.0000 | 60.0000 | 110.0000 | 80.0000 | 60.0000 | 70.0000 |
| 4RA-MVC | 90.0000 | 110.0000 | 70.0000 | 100.0000 | 90.0000 | 70.0000 | 70.0000 |
| 5RA-SVC | 80.0000 | 100.0000 | 70.0000 | 90.0000 | 80.0000 | 60.0000 | 60.0000 |
| 6 | | | | | | | |
| 7Mean | 88.0000 | 108.0000 | 78.0000 | 104.0000 | 94.0000 | 76.0000 | 76.0000 |
| 8SD | 14.8324 | 8.3666 | 16.4317 | 11.4018 | 15.1658 | 18.1659 | 13.4164 |
| 9SEM | 6.6332 | 3.7417 | 7.3485 | 5.0990 | 6.7823 | 8.1240 | 6.0000 |

Effective Refractory Period (ERP) dispersion (disp) (5 sites, dog8)

| -1- ERPdisp | -2- Bas | -3- V-D | -4- V1-S1 | -5- (V + )S-D | -6- S-S10 | -7- V2-S1 | -8- V-S1 + S-S10 |
|---|---|---|---|---|---|---|---|
| 1RA-app | 110.0000 | 110.0000 | 100.0000 | 110.0000 | 110.0000 | 90.0000 | 90.0000 |
| 2LA-app | 90.0000 | 100.0000 | 80.0000 | 100.0000 | 100.0000 | 90.0000 | 90.0000 |
| 3RA-IVC | 70.0000 | 90.0000 | 60.0000 | 100.0000 | 90.0000 | 70.0000 | 60.0000 |
| 4RA-MVC | 80.0000 | 90.0000 | 70.0000 | 100.0000 | 90.0000 | 70.0000 | 70.0000 |
| 5RA-SVC | 100.0000 | 110.0000 | 70.0000 | 120.0000 | 80.0000 | 70.0000 | 70.0000 |
| 6 | | | | | | | |
| 7Mean | 90.0000 | 100.0000 | 76.0000 | 106.0000 | 94.0000 | 78.0000 | 76.0000 |
| 8SD | 15.8114 | 10.0000 | 15.1658 | 8.9443 | 11.4018 | 10.9545 | 13.4164 |
| 9SEM | 7.0711 | 4.4721 | 6.7823 | 4.0000 | 5.0990 | 4.8990 | 6.0000 |

TABLE 3-continued

Effective Refractory Period (ERP) dispersion (disp) (5 sites, dog9)

| -1-<br>ERPdisp | -2-<br>Bas | -3-<br>V-D | -4-<br>V1-S1 | -5-<br>(V + )S-D | -6-<br>S-S10 | -7-<br>V2-S1 | -8-<br>V-S1 + S-S10 |
|---|---|---|---|---|---|---|---|
| 1RA-app | 90.0000 | 100.0000 | 90.0000 | 120.0000 | 100.0000 | 90.0000 | 90.0000 |
| 2LA-app | 100.0000 | 100.0000 | 100.0000 | 100.0000 | 100.0000 | 90.0000 | 100.0000 |
| 3RA-IVC | 80.0000 | 100.0000 | 70.0000 | 100.0000 | 100.0000 | 70.0000 | 70.0000 |
| 4RA-MVC | 80.0000 | 110.0000 | 60.0000 | 110.0000 | 100.0000 | 60.0000 | 50.0000 |
| 5RA-SVC | 70.0000 | 90.0000 | 60.0000 | 80.0000 | 80.0000 | 60.0000 | 70.0000 |
| 6 | | | | | | | |
| 7Mean | 84.0000 | 100.0000 | 76.0000 | 102.0000 | 96.0000 | 74.0000 | 76.0000 |
| 8SD | 11.4018 | 7.0711 | 18.1659 | 14.8324 | 8.9443 | 15.1658 | 19.4936 |
| 9SEM | 5.0990 | 3.1623 | 8.1240 | 6.6332 | 4.0000 | 6.7823 | 8.7178 |

Effective Refractory Period (ERP) dispersion (disp) (2 sites, dog10)

| -1-<br>ERPdisp | -2-<br>Bas | -3-<br>V-D | -4-<br>V1-S1 | -5-<br>(V + )S-D | -6-<br>S-S10 | -7-<br>V2-S1 | -8-<br>V-S1 + S-S10 |
|---|---|---|---|---|---|---|---|
| 1RA-app | 100.0000 | 110.0000 | 80.0000 | 100.0000 | 100.0000 | 80.0000 | 80.0000 |
| 2LA-app | 120.0000 | 120.0000 | 100.0000 | 120.0000 | 120.0000 | 100.0000 | 90.0000 |
| 3RA-IVC | | | | | | | |
| 4RA-MVC | | | | | | | |
| 5RA-SVC | | | | | | | |
| 6 | | | | | | | |
| 7Mean | 110.0000 | 115.0000 | 90.0000 | 110.0000 | 110.0000 | 90.0000 | 85.0000 |
| 8SD | 14.1421 | 7.0711 | 14.1421 | 14.1421 | 14.1421 | 14.1421 | 7.0711 |
| 9SEM | 10.0000 | 5.0000 | 10.0000 | 10.0000 | 10.0000 | 10.0000 | 5.0000 |

Effective Refractory Period (ERP) dispersion (disp) (5 sites, dog11)

| -1-<br>ERPdisp | -2-<br>Bas | -3-<br>V-D | -4-<br>V1-S1 | -5-<br>(V + )S-D | -6-<br>S-S10 | -7-<br>V2-S1 | -8-<br>V-S1 + S-S10 |
|---|---|---|---|---|---|---|---|
| 1RA-app | 120.0000 | 120.0000 | 110.0000 | 110.0000 | 110.0000 | 110.0000 | 110.0000 |
| 2LA-app | 110.0000 | 120.0000 | 100.0000 | 120.0000 | 110.0000 | 120.0000 | 100.0000 |
| 3RA-IVC | 100.0000 | 110.0000 | 80.0000 | 110.0000 | 100.0000 | 80.0000 | 80.0000 |
| 4RA-MVC | 80.0000 | 100.0000 | 70.0000 | 110.0000 | 100.0000 | 80.0000 | 60.0000 |
| 5RA-SVC | 80.0000 | 90.0000 | 70.0000 | 100.0000 | 90.0000 | 70.0000 | 60.0000 |
| 6 | | | | | | | |
| 7Mean | 98.0000 | 108.0000 | 86.0000 | 110.0000 | 102.0000 | 92.0000 | 82.0000 |
| 8SD | 17.8885 | 13.0384 | 18.1659 | 7.0711 | 8.3666 | 21.6795 | 22.8035 |
| 9SEM | 8.0000 | 5.8310 | 8.1240 | 3.1623 | 3.7417 | 9.6954 | 10.1980 |

Effective Refractory Period (ERP) dispersion (disp) (5 sites, dog12)

| -1-<br>ERPdisp | -2-<br>Bas | -3-<br>V-D | -4-<br>V1-S1 | -5-<br>(V + )S-D | -6-<br>S-S10 | -7-<br>V2-S1 | -8-<br>V-S1 + S-S10 |
|---|---|---|---|---|---|---|---|
| 1RA-app | 100.0000 | 100.0000 | 100.0000 | 100.0000 | 110.0000 | 90.0000 | 90.0000 |
| 2LA-app | 130.0000 | 130.0000 | 120.0000 | 140.0000 | 120.0000 | 110.0000 | 110.0000 |
| 3RA-IVC | 100.0000 | 110.0000 | 100.0000 | 120.0000 | 110.0000 | 100.0000 | 90.0000 |
| 4RA-MVC | 100.0000 | 110.0000 | 90.0000 | 120.0000 | 100.0000 | 80.0000 | 90.0000 |
| 5RA-SVC | 90.0000 | 110.0000 | 70.0000 | 100.0000 | 100.0000 | 70.0000 | 70.0000 |
| 6 | | | | | | | |
| 7Mean | 104.0000 | 112.0000 | 96.0000 | 116.0000 | 108.0000 | 90.0000 | 90.0000 |
| 8SD | 15.1658 | 10.9545 | 18.1659 | 16.7332 | 8.3666 | 15.8114 | 14.1421 |
| 9SEM | 6.7823 | 4.8990 | 8.1240 | 7.4833 | 3.7417 | 7.0711 | 6.3246 |

Effective Refractory Period (ERP) dispersion (disp) (5 sites, dog13)

| -1-<br>ERPdisp | -2-<br>Bas | -3-<br>V-D | -4-<br>V1-S1 | -5-<br>(V + )S-D | -6-<br>S-S10 | -7-<br>V2-S1 | -8-<br>V-S1 + S-S10 |
|---|---|---|---|---|---|---|---|
| 1RA-app | 80.0000 | 90.0000 | 80.0000 | 90.0000 | 90.0000 | 80.0000 | 80.0000 |
| 2LA-app | 90.0000 | 90.0000 | 80.0000 | 100.0000 | 90.0000 | 70.0000 | 80.0000 |
| 3RA-IVC | 80.0000 | 80.0000 | 70.0000 | 90.0000 | 80.0000 | 70.0000 | 70.0000 |
| 4RA-MVC | 70.0000 | 80.0000 | 60.0000 | 80.0000 | 80.0000 | 60.0000 | 60.0000 |
| 5RA-SVC | 60.0000 | 70.0000 | 40.0000 | 80.0000 | 70.0000 | 50.0000 | 60.0000 |
| 6 | | | | | | | |
| 7Mean | 76.0000 | 82.0000 | 66.0000 | 88.0000 | 82.0000 | 66.0000 | 70.0000 |
| 8SD | 11.4018 | 8.3666 | 16.7332 | 8.3666 | 8.3666 | 11.4018 | 10.0000 |
| 9SEM | 5.0990 | 3.7417 | 7.4833 | 3.7417 | 3.7417 | 5.0990 | 4.4721 |

TABLE 3-continued

Effective Refractory Period (ERP) dispersion (disp) (5 sites, dog14)

| -1-<br>ERPdisp | -2-<br>Bas | -3-<br>V-D | -4-<br>V1-S1 | -5-<br>(V + )S-D | -6-<br>S-S10 | -7-<br>V2-S1 | -8-<br>V-S1 + S-S10 |
|---|---|---|---|---|---|---|---|
| 1RA-app | 130.0000 | 130.0000 | 120.0000 | 130.0000 | 120.0000 | 120.0000 | 120.0000 |
| 2LA-app | 130.0000 | 130.0000 | 130.0000 | 130.0000 | 120.0000 | 120.0000 | 110.0000 |
| 3RA-IVC | 110.0000 | 120.0000 | 100.0000 | 130.0000 | 120.0000 | 100.0000 | 100.0000 |
| 4RA-MVC | 100.0000 | 120.0000 | 90.0000 | 120.0000 | 110.0000 | 90.0000 | 90.0000 |
| 5RA-SVC | 90.0000 | 100.0000 | 80.0000 | 110.0000 | 100.0000 | 80.0000 | 80.0000 |
| 6 | | | | | | | |
| 7Mean | 112.0000 | 120.0000 | 104.0000 | 124.0000 | 114.0000 | 102.0000 | 100.0000 |
| 8SD | 17.8885 | 12.2474 | 20.7364 | 8.9443 | 8.9443 | 17.8885 | 15.8114 |
| 9SEM | 8.0000 | 5.4772 | 9.2736 | 4.0000 | 4.0000 | 8.0000 | 7.0711 |

Effects of Autonomic Nervous System on Conduction Velocity

| | -1-<br>Dogs # | -2-<br>Bas | -3-<br>V-D | -4-<br>V1-S1 | -5-<br>(V + S)-D | -6-<br>S-S10 | -7-<br>V2-S1 | -8-<br>V-S1 + S-S10 |
|---|---|---|---|---|---|---|---|---|
| 1 | 2.0000 | 91.3000 | 87.3000 | 102.5000 | 90.0000 | 84.0000 | 100.0000 | 106.0000 |
| 2 | 3.0000 | 100.0000 | 101.0000 | 100.0000 | 97.0000 | 100.0000 | 102.0000 | 108.0000 |
| 3 | 4.0000 | 97.0000 | 90.0000 | 98.0000 | 87.0000 | 88.0000 | 108.0000 | 112.0000 |
| 4 | 5.0000 | 96.5000 | 88.5000 | 107.0000 | 96.0000 | 104.0000 | 111.0000 | 117.0000 |
| 5 | 6.0000 | 87.9000 | 80.0000 | 96.0000 | 82.0000 | 84.0000 | 91.0000 | 96.0000 |
| 6 | 7.0000 | 70.5000 | 70.5000 | 87.0000 | 73.0000 | 78.0000 | 86.0000 | 93.0000 |
| 7 | 8.0000 | 121.0000 | 102.0000 | 118.0000 | 94.0000 | 98.0000 | 125.0000 | 120.0000 |
| 8 | 9.0000 | 96.4000 | 86.0000 | 104.0000 | 90.0000 | 94.0000 | 111.0000 | 116.0000 |
| 9 | 11.0000 | 100.9000 | 88.0000 | 14.0000 | 84.0000 | 95.0000 | 112.0000 | 124.0000 |
| 10 | 12.0000 | 88.5000 | 76.0000 | 98.0000 | 70.0000 | 77.0000 | 108.0000 | 114.0000 |
| 11 | 13.0000 | 130.0000 | 110.0000 | 138.0000 | 104.0000 | 120.0000 | 148.0000 | 150.0000 |
| 12 | 14.0000 | 117.0000 | 102.0000 | 128.0000 | 98.0000 | 115.0000 | 124.0000 | 128.0000 |
| 13 | | | | | | | | |
| 14 | | | | | | | | |
| 15 | | | | | | | | |
| 16Mean | | 99.7500 | 90.1083 | 107.5417 | 88.7500 | 94.7500 | 110.5000 | 115.3333 |
| 17SD | | 16.2957 | 11.7344 | 14.5531 | 10.1813 | 13.6323 | 16.4510 | 15.0414 |
| 18SEM | | 4.6782 | 3.3874 | 4.2011 | 2.9391 | 3.9353 | 4.7490 | 4.3421 |

One Way Repeated Measures Analysis of Variance

| Normality Test: | Passed | (P = 0.6112) | | | |
|---|---|---|---|---|---|
| Equal Variance Test: | Passed | (P = 0.3313) | | | |
| Group | N | Missing | Mean | Std Dev | SEM |
| Bas | 12 | 0 | 99.8 | 16.2 | 4.68 |
| V-D | 12 | 0 | 90.1 | 11.7 | 3.39 |
| V1-S1 | 12 | 0 | 107.5 | 14.6 | 4.20 |
| (V + S)-D | 12 | 0 | 88.8 | 10.2 | 2.94 |
| S-S10 | 12 | 0 | 94.8 | 13.6 | 3.94 |
| V2-S1 | 12 | 0 | 110.5 | 16.5 | 4.75 |
| V-S1 + S-S10 | 12 | 0 | 115.3 | 15.0 | 4.34 |

Power of performed test with alpha 0.0500: 1.0000

| Source of Variance | DF | SS | MS | F | P |
|---|---|---|---|---|---|
| Between Subjects | 11 | 13221.5 | 1202.0 | | |
| Between Treatments | 6 | 7773.5 | 1295.6 | 39.6 | 5.14E-020 |
| Residual | 66 | 2162.0 | 32.8 | | |
| Total | 83 | 23156.9 | | | |

The differences in the mean values among the treatment groups are greater than would be expected by chance; there is a statistically significant difference (P = 5.14E-020). To isolate the group or groups that differ from the others use a multiple comparison procedure.

All Pairwise Multiple Comparison Procedures (Bonferroni's method):

| Comparison | Diff of Means | t | P < 0.05 |
|---|---|---|---|
| Bas vs V-S1 + S-S10 | −15.58 | −6.669 | Yes |
| Bas vs V2-S1 | −10.75 | −4.601 | Yes |
| Bas vs S-S10 | 5.00 | 2.140 | No |
| Bas vs (V + S)-D | 11.00 | 4.708 | Yes |
| Bas vs V1-S1 | −7.79 | −3.335 | Yes |
| Bas vs V-D | 9.64 | 4.126 | Yes |
| V-D vs V-S1 + S-S10 | −25.22 | −10.796 | Yes |
| V-D vs V2-S1 | −20.39 | −8.727 | Yes |
| V-D vs S-S10 | −4.64 | −1.987 | No |
| V-D vs (V + S)-D | 1.36 | 0.581 | No |

TABLE 3-continued

| | | | |
|---|---|---|---|
| V-D vs V1-S1 | −17.43 | −7.461 | Yes |
| V1-S1 vs V-S1 + S-S10 | −7.79 | −3.335 | Yes |
| V1-S1 vs V2-S1 | −2.96 | −1.266 | No |
| V1-S1 vs S-S10 | 12.79 | 5.475 | Yes |
| V1-S1 vs (V + S)-D | 18.79 | 8.042 | Yes |
| (V + S)-D vs V-S1 + S-S10 | −26.58 | −11.377 | Yes |
| (V + S)-D vs V2-S1 | −21.75 | −9.309 | Yes |
| (V + S)-D vs S-S10 | −6.00 | −2.568 | No |
| S-S10 vs V-S1 + S-S10 | −20.58 | −8.809 | Yes |
| S-S10 vs V2-S1 | −15.75 | −6.741 | Yes |
| V2-S1 vs V-S1 + S-S10 | −4.83 | −2.069 | No |

Effects of Autonomic Nervous System on the Wavelength

| -1-<br>Dogs # | -2-<br>Bas | -3-<br>V-D | -4-<br>V1-S1 | -5-<br>(V + S)-D | -6-<br>S-S10 | -7-<br>V2-S1 | -8-<br>V-S1 + S-S10 |
|---|---|---|---|---|---|---|---|
| 1 | 2.0000 | 9.5000 | 9.4000 | 10.0000 | 10.0000 | 9.1000 | 10.0000 | 10.2000 |
| 2 | 3.0000 | 8.5000 | 9.4000 | 7.3000 | 9.5000 | 8.8000 | 8.0000 | 8.1000 |
| 3 | 4.0000 | 11.6000 | 11.3000 | 10.3000 | 10.4000 | 9.9000 | 11.3000 | 11.2000 |
| 4 | 5.0000 | 12.0000 | 11.5000 | 12.6000 | 12.9000 | 12.5000 | 13.3000 | 12.6000 |
| 5 | 6.0000 | 8.2000 | 9.4000 | 7.7000 | 10.7000 | 7.8000 | 7.6000 | |
| 6 | 7.0000 | 6.2000 | 7.6000 | 6.8000 | 7.6000 | 7.3000 | 6.6000 | 7.7000 |
| 7 | 8.0000 | 10.9000 | 10.2000 | 9.0000 | 10.0000 | 9.2000 | 9.8000 | 9.1000 |
| 8 | 9.0000 | 8.1000 | 8.6000 | 7.9000 | 9.2000 | 9.0000 | 8.2000 | 8.8000 |
| 9 | 11.0000 | 9.9000 | 9.5000 | 9.8000 | 9.2000 | 9.7000 | 10.3000 | 10.2000 |
| 10 | 12.0000 | 9.2000 | 8.5000 | 9.4000 | 8.1000 | 8.3000 | 9.7000 | 10.3000 |
| 11 | 13.0000 | 9.9000 | 9.0000 | 9.1000 | 9.2000 | 9.8000 | 9.8000 | 10.5000 |
| 12 | 14.0000 | 13.1000 | 12.2000 | 13.3000 | 12.2000 | 13.1000 | 12.6000 | 12.8000 |
| 13 | | | | | | | | |
| 14 | | | | | | | | |
| 15 | | | | | | | | |
| 16Mean | | 9.7583 | 9.7167 | 9.4333 | 9.9167 | 9.5417 | 9.7667 | 10.1364 |
| 17SD | | 1.9242 | 1.3537 | 1.9846 | 1.5183 | 1.7159 | 1.9888 | 1.6555 |
| 18SEM | | 0.5555 | 0.3908 | 0.5729 | 0.4383 | 0.4954 | 0.5741 | 0.4991 |

One Way Repeated Measures Analysis of Variance

| | | | | | |
|---|---|---|---|---|---|
| Normality Test: | Passed | (P = 0.7307) | | | |
| Equal Variance Test: | Passed | (P = 0.7441) | | | |
| Group | N | Missing | Mean | Std Dev | SEM |
| Bas | 12 | 0 | 9.76 | 1.92 | 0.555 |
| V-D | 12 | 0 | 9.72 | 1.35 | 0.391 |
| V1-S1 | 12 | 0 | 9.43 | 1.98 | 0.573 |
| (V + S)-D | 12 | 0 | 9.92 | 1.52 | 0.438 |
| S-S10 | 12 | 0 | 9.54 | 1.72 | 0.495 |
| V2-S1 | 12 | 0 | 9.77 | 1.99 | 0.574 |
| V-S1 + S-S10 | 12 | 1 | 10.14 | 1.66 | 0.499 |

Power of performed test with alpha 0.0500: 1.0000
The power of the performed test (0.0793) is below the desired power of 0.8000. You should interpret the negative findings cautiously.

| Source of Variance | DF | SS | MS | F | P |
|---|---|---|---|---|---|
| Between Subjects | 11 | 204.77 | 18.616 | | |
| Between Treatments | 6 | 2.93 | 0.489 | 1.13 | 0.355 |
| Residual | 65 | 28.10 | 0.432 | | |
| Total | 82 | 236.59 | 2.885 | | |

The differences in the mean values among the treatment groups are not great enough to exclude the possibility that the difference is due to random sampling variability; there is not a statistically significant difference (P = 0.355).
Expected Mean Squares:

Approximate DF--Residual = 65.0
E{MS(Subj)} = var(res) + 6.91 var(Subj)
E{MS(Treatment)} = var(res) + var(Treatment)
E{MS(Residual)} = var(res)

CONCLUSION

Parasympathetic system nervous denervation significantly decreased the occurrence of atrial fibrillation. However, the activation of parasympathetic nervous system significantly increased the occurrence of atrial fibrillation and predominated the sympathetic nervous system activation effects. Local parasympathetic neurotransmitters infusion significantly increased the conversion of sustained atrial flutter to non sustained atrial fibrillation, and then to sinus rhythm. Furthermore, the local parasympathetic neurotransmitters infusion significantly reversed the effects of sotalol, a class 3 antiarrhythmic drug, on the reentry circuit characteristics during a sustained atrial flutter. This invention determined the significant effects of parasympathetic nervous system activation on the occurrence of atrial re-entrant arrhythmias. Furthermore, this invention illustrated the necessity of local ablation method of the atrial areas with the greatest density of parasympathetic innervation for the treatment of atrial arrhythmias, such as the areas near the sinoatrial nodal fat pad and septal.

What is claimed is:

1. A method comprising the step of inhibiting the effects of the parasympathetic nervous system neurotransmitter release on the atria, wherein said method converting and prevents atrial flutter and fibrillation.

2. A method comprising the step of locally infusing the parasympathetic neurotransmitter, wherein said method significantly increases the conversion of sustained atrial flutter to non sustained atrial fibrillation.

3. A method comprising the step of local infusing the parasympathetic neurotransmitter during a sustained atrial flutter, wherein said method significantly reverses the antiarrhythmic effects of a class 3 antiarrhythmic drug, sotalol.

4. The method, according to anyone of claims 2 or 3, wherein infusing a parasympathetic nervous system blocker significantly preserves the antiarrhythmic effects of class 3 antiarrhythmic drugs on the occurrence of a sustained atrial re-entrant arrhythmias.

5. The method, according to anyone of claims 2 or 3, wherein infusing a parasympathetic nervous system blocker significantly preserves the antiarrhythmic effects of class I, II, IV, V or any other drugs used for the treatment of any of atrial re-entrant arrhythmias.

6. A method of treating atrial fibrillation and flutter, wherein delivering an anticholinergic agent to the myocardium significantly converts and prevents the occurrence of atrial flutter and fibrillation comprising at least one of:

a) infusing drug via the coronary arteries, b) a direct application via drug eluting patch on the atrial epicardium, c) a direct application via drug eluting catheter on the atrial endocardium.

7. A method, wherein catheter ablation of the atria in areas with the greatest density of parasympathetic nerve innervation significantly converts and prevents the occurrence of atrial fibrillation and flutter or other re-entrant atrial arrhythmias comprising:

inserting an electrophysiologic ablation catheter having a tip section with an ablation electrode into the right or left atrial chambers and directing the catheter to endomyocardial locations with high density of the parasympathetic fibers;

stabilizing the ablation electrode at said myocardium location;

delivering effective ablation energy through the electrode sufficient to destroy the parasympathetic nerve fibers in order to eliminate their neurotransmitter effects in the atria.

8. The method, according to claims 3 or 7, wherein catheter ablation of the atria in areas with the greatest density of parasympathetic nerve innervation significantly preserves and enhances the antiarrhythmic effects of any drugs used for the treatment of atrial arrhythmias.

* * * * *